United States Patent [19]

Pieper et al.

[11] Patent Number: 5,700,801

[45] Date of Patent: Dec. 23, 1997

[54] PIPERAZINE DERIVATIVES, PHARMACEUTICAL COMPOSITIONS CONTAINING THESE COMPOUNDS, THEIR USE AND PROCESSES FOR PREPARING THEM

[75] Inventors: Helmut Pieper; Volkhard Austel, both of Biberach; Frank Himmelsbach; Günter Linz, both of Mittelbiberach; Brian Guth, Warthausen; Johannes Weisenberger, Biberach, all of Germany

[73] Assignee: Karl Thomae, GmbH, Biberach An Der Riss, Germany

[21] Appl. No.: 572,256

[22] Filed: Dec. 13, 1995

[30] Foreign Application Priority Data

Dec. 23, 1994 [DE] Germany .......................... 44 46 300.6
Sep. 8, 1995 [DE] Germany .......................... 195 33 224.5

[51] Int. Cl.$^6$ .................. C07D 213/74; C07D 401/12; C07D 211/18; A61K 31/495
[52] U.S. Cl. .................. 514/252; 544/360; 544/365
[58] Field of Search .................. 544/360, 364; 514/252

[56] References Cited

U.S. PATENT DOCUMENTS

| 4,539,322 | 9/1985 | Campbell et al. ........ 514/495 |
| 4,895,846 | 1/1990 | Poindexter et al. ........ 514/252 |
| 5,196,428 | 3/1993 | Meanwell . | |

FOREIGN PATENT DOCUMENTS

| 0 074 768 | 3/1983 | European Pat. Off. . |
| 0 233 051 | 8/1987 | European Pat. Off. . |
| 0 330 065 | 8/1989 | European Pat. Off. . |
| 0 350 145 | 1/1990 | European Pat. Off. . |
| 33 02 021 | 7/1984 | Germany . |
| WO 94 22834 | 10/1994 | WIPO . |
| WO 94 22835 | 10/1994 | WIPO . |

OTHER PUBLICATIONS

Alberto et al. J. Med. Chem. (1987), 30, 13–19.

*Primary Examiner*—Mukund J. Shah
*Assistant Examiner*—Sabiha Qazi
*Attorney, Agent, or Firm*—Robert P. Raymond; Alan R. Stempel; Mary-Ellen Devlin

[57] ABSTRACT

Piperazine derivatives useful in the treatment or prevention of inflammation, bone degradation, thrombosis and tumor metastasis. Exemplary species are:

(a) [4-trans-[3-[4-(4-Pyridyl)-piperazin-1-yl]propionyl]amino]-cyclohexanecarboxylic acid,
(b) 3-[4-trans-[4-(4-Pyridyl)-piperazin-1-yl]carbonylamino]-cyclohexylpropionic acid,
(c) 3-[4-trans-[4-(4-Pyridyl)-piperazin-1-yl]malonylamino]cyclohexylcarboxylic acid,
(d) Methyl [4-trans-[3-[4-(4-pyridyl)-piperazin-1-yl]propionyl]-amino]cyclohexane carboxylate,
(e) Methyl 3-[4-trans-[4-(4-pyridyl)-piperazin-1-yl]carbonylamino]cyclohexyl propionate,
(f) Methyl [4-trans-[4-(4-pyridyl)-piperazin-1-yl]malonylamino]-cyclohexyl carboxylate,
(g) Cyclohexyl [4-trans-[[4-(4-pyridyl)-piperazin-1-yl]acetyl]-amino-cyclohexane carboxylate, and
(h) Isobutyl [4-trans-[[4-(4-pyridyl)-piperazin-1-yl]-acetyl]amino]-cyclohexane carboxylate.

11 Claims, No Drawings

PIPERAZINE DERIVATIVES, PHARMACEUTICAL COMPOSITIONS CONTAINING THESE COMPOUNDS, THEIR USE AND PROCESSES FOR PREPARING THEM

The present invention relates to piperazine derivatives of the general formula

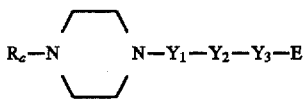

(I)

the tautomers, stereoisomers, including mixtures thereof, and the salts thereof, particularly the salts with physiologically acceptable acids or bases which have valuable pharmacological properties, preferably aggregation-inhibiting effects, pharmaceutical compositions containing these compounds and the use thereof as well as processes for preparing them.

In general formula I above, with the proviso that, if $R_a$ denotes a 4-pyridyl group, it is not possible simultaneously for (a) $Y_1$ to denote a —$CH_2CO$—, —$CH(CH_3)CO$—, —$C(CH_3)_2CO$—, —$CH_2CH_2CO$— or —$CH_2CH(CH_3)CO$— group, $Y_2$ to denote a 1,3- or 1,4-phenylene group, $Y_3$ to denote a —$CH_2CO$—, —$CH_2CH_2CO$— or —$OCH_2CO$— group and E to denote a hydroxy, methoxy or ethoxy group or (b) for $Y_1$ to denote —$CH_2CO$— group, $Y_2$ to denote a 3- or 4-piperidinylene group, $Y_3$ to denote a —$CO$—, —$CH_2CO$— or —$OCH_2CO$— group and for E to denote a hydroxy or ethoxy group, (c) for $Y_1$ to denote a —$COCH_2$— group, $Y_2$ to denote a 1,4-phenylene group, $Y_3$ to denote an —$OCH_2CO$— group and E to denote a hydroxy or tert.butyloxy group, $R_a$ denotes a pyridyl group, $Y_1$ denotes a —$CO$—, —$CO$—$CO$—, —$A_1$—$CO$—, —$CO$—$A_1$—, —$SO_2$—$A_2$—, —$A_2$—$SO_2$—, —$CO$—$A_1$—$CO$—, —$CO$—$NR_1$—$CO$—, —$CO$—$NR_1$—$A_2$—, —$CO$—$NR_1$—$A_2$—$CO$— or —$CO$—$A_2$—$NR_1$—$CO$— group, wherein $R_1$ denotes a hydrogen atom, a $C_{1-5}$-alkyl-, aryl- or aryl-$C_{1-3}$-alkyl group, $A_1$ denotes an n-$C_{1-5}$-alkylene group optionally substituted by a $C_{1-5}$-alkyl-, cyclohexyl-$C_{1-3}$-alkyl-, aryl- or aryl-$C_{1-3}$-alkyl group or an $R_1O$— group, provided that this is not in the α-position to a nitrogen atom, and $A_2$ denotes an n-$C_{1-4}$-alkylene group optionally substituted by a $C_{1-5}$-alkyl, aryl or aryl-$C_{1-3}$-alkyl group, $Y_2$ denotes a phenylene, cyclohexylene or pyridinylene group, a 3-piperidinylene, 4-piperidinylene or 1,4-piperazinylene group wherein one or two methylene groups adjacent to a nitrogen atom may be replaced by a carbonyl group, or $Y_2$ denotes an —$NR_1$—B— or —O—B— group, the link to the $Y_1$ group being effected via the nitrogen atom of the —$NR_1$— group or via the oxygen atom of the —O—B— group, wherein $R_1$ is as hereinbefore defined and B denotes a phenylene, cyclohexylene, piperidinylene or pyridinylene group, the piperidinylene group being linked via the 3- or 4-position to the group —$NR_1$— or to the oxygen atom, and wherein additionally a methylene group adjacent to a nitrogen atom may be replaced by a carbonyl group, $Y_3$ denotes a —$CO$—, —$A_2$—$CO$—, —$CH_2$—$CH(NHR_2)$—$CO$—, —$NR_2$—$A_3$—$CO$—, —O—$A_3$—$CO$— or —$CO$—$A_3$—$CO$— group, wherein $R_1$ and $A_2$ are as hereinbefore defined, $A_3$ denotes an n-$C_{1-3}$-alkylene group optionally substituted by a $C_{1-5}$-alkyl, aryl or aryl-$C_{1-3}$-alkyl group and $R_2$ denotes a hydrogen atom, a $C_{1-5}$-alkyl, aryl-$C_{1-3}$-alkyl, aryl, $C_{1-5}$-alkoxycarbonyl, $C_{1-5}$-alkanoyl, $C_{1-5}$-alkylsulphonyl, aryl-$C_{1-3}$-alkylsulphonyl or arylsulphonyl group, a formyl group optionally substituted by an aryl- or aryl-$C_{1-3}$-alkyl group, and the —$A_2$—$CO$— group is linked to the group $Y_2$ via the group $A_2$, the —$NR_2$—$A_3$—$CO$— group is linked to the group $Y_2$ via the —$NR_2$— group and the —O—$A_3$—$CO$— group is linked to the group $Y_2$ via the oxygen atom, but an —$NR_2$— or —O—$A_3$—$CO$— group cannot be linked to a nitrogen atom of the group $Y_2$, and E denotes a hydroxy group, a $C_{1-6}$-alkoxy group, a phenylalkoxy group wherein the alkoxy moiety may contain 1 to 3 carbon atoms, a $C_{3-9}$-cycloalkoxy group, wherein the $C_{5-8}$-cycloalkyl moiety may additionally be substituted by one or two $C_{1-3}$-alkyl groups, a $C_{5-8}$-cycloalkoxy group wherein a methylene group in the 3- or 4-position of the cycloalkyl moiety is substituted by an oxygen atom or by an imino group optionally substituted by an alkyl, phenylalkyl or phenylalkoxycarbonyl group, wherein the alkyl and alkoxy moieties may each contain 1 to 3 carbon atoms, or by a $C_{2-6}$-alkanoyl group, and the cycloalkyl moiety may additionally be substituted by one or two $C_{1-3}$-alkyl groups, a cycloalkenyloxy group wherein the cycloalkenyl moiety may contain 4 to 7 carbon atoms, an alkenyloxy, phenylalkenyloxy, alkynyloxy or phenylalkynyloxy group, with the proviso that no bond to the oxygen atom starts from a carbon atom carrying a double or triple bond, and wherein the alkenyl and alkynyl moieties may each contain 3 to 5 carbon atoms, a cycloalkylalkoxy group, wherein the cycloalkyl moiety may contain 3 to 8 carbon atoms and the alkoxy moiety may contain 1 to 3 carbon atoms, a bicycloalkoxy group having a total of 8 to 10 carbon atoms which may additionally be substituted in the bicycloalkyl moiety by one or two $C_{1-3}$-alkyl groups, a 1,3-dihydro-3-oxo-1-isobenzofuranyloxy group or an $R_5$—$CO$—O—($R_3CR_4$)—O— group, wherein $R_3$ denotes a hydrogen atom, a $C_{1-6}$-alkyl, $C_{3-7}$-cycloalkyl or phenyl group, $R_4$ denotes a hydrogen atom or a $C_{1-6}$-alkyl group and $R_5$ denotes a $C_{1-5}$-alkyl, $C_{1-5}$-alkoxy, $C_{5-7}$-cycloalkyl or $C_{5-7}$-cycloalkoxy group, or E denotes an α-amino group of a natural amino acid and the esters thereof.

By the terms "an aryl group", "a phenyl group" or "a phenylene group" mentioned in the definitions of the above groups, is meant in particular a phenyl or phenylene group optionally mono-, di- or trisubstituted by fluorine, chlorine, bromine or iodine atoms, or by alkyl, trifluoromethyl, nitro, amino, alkylamino, dialkylamino, alkanoylamino, hydroxy, alkoxy, carboxy, alkoxycarbonyl, hydroxycarbonylalkoxy, alkoxycarbonylalkoxy, aminocarbonyl, alkylaminocarbonyl or dialkylaminocarbonyl groups, wherein the substituents may be identical or different and the above-mentioned alkyl and alkoxy moieties may each contain 1 to 3 carbon atoms, and by the esters of a natural α-amino group are meant the $C_{1-6}$-alkyl, $C_{2-6}$-alkenyl, $C_{5-7}$-cycloalkyl, phenyl or phenyl-$C_{1-3}$-alkyl esters such as the methyl, ethyl, n-propyl, isopropyl, tert.butyl, allyl, phenyl or benzyl esters.

Preferred compounds of the above general formula I are those wherein with the proviso that, if $R_a$ denotes a 4-pyridyl group, it is not possible simultaneously for (a) $Y_1$ to denote a $-CH_2CO-$, $-CH(CH_3)CO-$, $-C(CH_3)_2CO-$, $-CH_2CH_2CO-$ or $-CH_2CH(CH_3)CO-$ group, $Y_2$ to denote a 1,3- or 1,4-phenylene group, $Y_3$ to denote a $-CH_2CO-$, $-CH_2CH_2CO-$ or $-OCH_2CO-$ group and E to denote a hydroxy, methoxy or ethoxy group or (b) for $Y_1$ to denote a $-CH_2CO-$ group, $Y_2$ to denote a 3- or 4-piperidinylene group, $Y_3$ to denote a $-CO-$, $-CH_2CO-$ or $-OCH_2CO-$ group and E to denote a hydroxy or ethoxy group, (c) $Y_1$ to denote a $-COCH_2-$ group, $Y_2$ to denote a 1,4-phenylene group, $Y_3$ to denote an $-OCH_2CO-$ group and E to denote a hydroxy or tert.butyloxy group, $R_a$ denotes a 3- or 4-pyridyl group, $Y_1$ denotes a $-CO-$, $-CO-CO-$, $-A_1-CO-$, $-CO-A_1-$ or $-CO-A_1-CO-$ group, wherein $A_1$ denotes an n-$C_{1-5}$-alkylene group optionally substituted by a $C_{1-5}$-alkyl, phenyl or phenyl-$C_{1-3}$-alkyl group, wherein the phenyl nuclei of the above-mentioned phenyl and phenylalkyl groups may each additionally be substituted by a hydroxy or methoxy group, $Y_2$ denotes a 1,3-phenylene, 1,4-phenylene, 3-piperidinylene, 4-piperidinylene, 1,4-piperazinylene or $-NR_1-B-$ group, the link to the $Y_1$ group being effected via the nitrogen atom of the $-NR_1-$ group and $R_1$ denotes a hydrogen atom, a $C_{1-5}$-alkyl, phenyl or phenyl-$C_{1-3}$-alkyl group and B denotes a 1,3-phenylene, 1,4-phenylene, 1,3-cyclohexylene, 1,4-cyclohexylene, 3-piperidinylene or 4-piperidinylene group, $Y_3$ denotes a $-CO-$, $-A_2-CO-$, $-NR_2-A_3-CO-$ or $-O-A_3-CO-$ group, wherein $A_2$ denotes an n-$C_{1-4}$-alkylene group optionally substituted by a $C_{1-5}$-alkyl, phenyl or phenyl-$C_{1-3}$-alkyl group, $A_3$ denotes an n-$C_{1-3}$-alkylene group optionally substituted by a $C_{1-5}$-alkyl, phenyl or phenyl-$C_{1-3}$-alkyl group and $R_2$ denotes a hydrogen atom, a $C_{1-5}$-alkyl, phenyl-$C_{1-3}$-alkyl, phenyl, $C_{1-5}$-alkoxycarbonyl or $C_{1-5}$-alkanoyl group, and the $-A_2-CO-$ group is linked to the group $Y_2$ via the group $A_2$, the $-NR_2-A_3-CO-$ group is linked to the group $Y_2$ via the $-NR_2-$ group and the $-O-A_3-CO-$ group is linked to the group $Y_2$ via the oxygen atom, but an $-NR_2-$ or $-O-A_3-CO-$ group may not be linked to a nitrogen atom of the group $Y_2$, and E denotes a hydroxy group, a $C_{1-6}$-alkoxy group, a phenylalkoxy group wherein the alkoxy moiety may contain 1 to 3 carbon atoms, a $C_{4-7}$-cycloalkoxy group or an $R_5-CO-O-(R_3CR_4)-O-$ group wherein $R_3$ denotes a hydrogen atom, a $C_{1-6}$-alkyl, $C_{3-7}$-cycloalkyl or phenyl group, $R_4$ denotes a hydrogen atom or a $C_{1-6}$-alkyl group and $R_5$ denotes a $C_{1-5}$-alkyl, $C_{1-5}$-alkoxy, $C_{5-7}$-cycloalkyl or $C_{5-7}$-cycloalkoxy group, or E denotes an α-amino group of a natural amino acid or the esters thereof, the tautomers, the stereoisomers, including mixtures thereof, and the salts thereof.

Particularly preferred compounds of general formula I above are those wherein, with the proviso that it is not possible simultaneously for (a) $Y_1$ to denote a $-CH_2CO-$, $-CH(CH_3)CO-$, $-C(CH_3)_2CO-$, $-CH_2CH_2CO-$ or $-CH_2CH(CH_3)CO-$ group, for $Y_2$ to denote a 1,3- or 1,4-phenylene group, $Y_3$ to denote a $-CH_2CO-$, $-CH_2CH_2CO-$ or $-OCH_2CO-$ group and E to denote a hydroxy, methoxy or ethoxy group or (b) for $Y_1$ to denote a $-CH_2CO-$ group, $Y_2$ to denote a 3- or 4-piperidinylene group, $Y_3$ to denote a $-CO-$, $-CH_2CO-$ or $-OCH_2CO-$ group and E to denote a hydroxy or ethoxy group, (c) for $Y_1$ to denote a $-COCH_2-$ group, $Y_2$ to denote a 1,4-phenylene group, $Y_3$ to denote an $-OCH_2CO-$ group and E to denote a hydroxy or tert.butyloxy group, $R_a$ denotes a 4-pyridyl group, $Y_1$ denotes a $-CO-$, $-CO-CO-$, $-A_1-CO-$, $-CO-A_1-$ or $-CO-A_1-CO-$ group, wherein $A_1$ denotes an n-$C_{1-5}$-alkylene group optionally substituted by a $C_{1-5}$-alkyl, phenyl or phenyl-$C_{1-2}$-alkyl group, wherein the phenyl nuclei of the above-mentioned phenyl and phenylalkyl groups may each additionally be substituted by a hydroxy or methoxy group, $Y_2$ denotes a 1,4-phenylene, 4-piperidinylene, 1,4-piperazinylene or $-NR_1-B-$ group, the $Y_1$ group being linked via the nitrogen atom of the $-NR_1-$ group and $R_1$ denotes a hydrogen atom, a $C_{1-5}$-alkyl, phenyl or phenyl-$C_{1-2}$-alkyl group and B denotes a 1,3-phenylene, 1,4-phenylene, 1,3-cyclohexylene, 1,4-cyclohexylene, 3-piperidinylene or 4-piperidinylene group, $Y_3$ denotes a $-CO-$, $-A_2-CO-$, $-NR_2-A_3-CO-$ or $-O-A_3-CO-$ group, wherein $A_2$ denotes an n-$C_{1-4}$-alkylene group optionally substituted by a $C_{1-3}$-alkyl, phenyl or phenyl-$C_{1-2}$-alkyl group, $A_3$ denotes an n-$C_{1-3}$-alkylene group optionally substituted by a $C_{1-5}$-alkyl, phenyl or phenyl-$C_{1-3}$-alkyl group and $R_2$ denotes a hydrogen atom, a $C_{1-3}$-alkyl, $C_{1-5}$-alkoxycarbonyl or $C_{1-3}$-alkanoyl group, and the $-A_2-CO-$ group is linked to the group $Y_2$ via the group $A_2$, the $-NR_2-A_3-CO-$ group is linked to the group $Y_2$ via the $-NR_2-$ group and the $-O-A_3-CO-$ group is linked to the group $Y_2$ via the oxygen atom, but an $-NR_2-$ or $-O-A_3-CO-$ group cannot be linked to a nitrogen atom of the group $Y_2$, and E denotes a hydroxy group, a $C_{1-5}$-alkoxy group, a $C_{5-7}$-cycloalkoxy group or an $R_5-CO-O-(R_3CR_4)-O-$ group, wherein $R_3$ denotes a hydrogen atom, a $C_{1-3}$-alkyl or $C_{5-7}$-cycloalkyl group, $R_4$ denotes a hydrogen atom and $R_5$ denotes a $C_{1-5}$-alkyl or $C_{1-3}$-alkoxy group, or E denotes an α-amino group of a natural amino acid or the esters thereof with a $C_{1-6}$-alkanol or benzylalcohol, the tautomers, the stereoisomers, including mixtures thereof, and the salts thereof.

Most particularly preferred compounds of the above general formula I are those wherein, with the proviso that it is not possible simultaneously for (a) $Y_1$ to denote a $-CH_2CO-$, $-CH(CH_3)CO-$, $-C(CH_3)_2CO-$, $-CH_2CH_2CO-$ or $-CH_2CH$ (CH$_3$)CO— group, for Y$_2$ to denote a 1,3- or 1,4-phenylene group, Y$_3$ to denote a —CH$_2$CO—, —CH$_2$CH$_2$CO— or —OCH$_2$CO— group and E to denote a hydroxy, methoxy or ethoxy group or (b) for Y$_1$ to denote a —CH$_2$CO— group, Y$_2$ to denote a 4-piperidinylene group, Y$_3$ to denote a —CO—, —CH$_2$CO— or —OCH$_2$CO— group and E to denote a hydroxy or ethoxy group, (c) for Y$_1$ to denote a —COCH$_2$— group, Y$_2$ to denote a 1,4-phenylene group, Y$_3$ to denote an —OCH$_2$CO— group and E to denote a hydroxy or tert.butyloxy group, R$_a$ denotes a 4-pyridyl group, Y$_1$ denotes a —CO—, —COCO—, —A$_1$—CO—, —CO—A$_1$— or —CO—CH$_2$—CO— group, wherein A$_1$ denotes an n-C$_{1-4}$-alkylene group optionally substituted by a methyl or methoxyphenyl group, Y$_2$ denotes a 1,4-phenylene, 4-piperidinylene, 1,4-piperazinylene or —NR$_1$—B— group, the link with the Y$_1$ group being effected via the nitrogen atom of the —NR$_1$— group and R$_1$ denotes a hydrogen atom and B denotes a 1,3-phenylene, 1,4-phenylene, 1,3-cyclohexylene, 1,4-cyclohexylene or 4-piperidinylene group, Y$_3$ denotes a —CO—, —A$_2$—CO—, —NR$_2$—A$_3$—CO— or —O—A$_3$—CO— group, wherein A$_2$ denotes an n-C$_{1-3}$-alkylene group, A$_3$ denotes a C$_{1-2}$-alkylene group and R$_2$ denotes a hydrogen atom, a methyl, benzyl, phenylethyl or acetyl group, and the —A$_2$—CO— group is linked to the group Y$_2$ via the group A$_2$, the —NR$_2$—A$_3$—CO— group is linked to the group Y$_2$ via the —NR$_2$— group and the —O—A$_3$—CO— group is linked to the group Y$_2$ via the oxygen atom, but an —NR$_2$— or —O—A$_3$—CO— group cannot be linked to a nitrogen atom of the group Y$_2$, and E denotes a hydroxy group, a C$_{1-4}$-alkoxy group, a C$_{5-7}$-cycloalkoxy group or an R$_5$—CO—O—(R$_3$CR$_4$)—O— group, wherein R$_3$ denotes a hydrogen atom or a C$_{1-3}$-alkyl group, R$_4$ denotes a hydrogen atom and R$_5$ denotes a C$_{1-5}$-alkyl or C$_{1-3}$-alkoxy group, or E denotes a glycinyl group or the methyl ester thereof, the tautomers, the stereoisomers, including mixtures thereof, and the salts thereof.

The following are examples of particularly useful compounds:

(a) [4-trans-[3-[4-(4 -Pyridyl)-piperazin-1-yl]propionyl] amino]-cyclohexanecarboxylic acid, (b) 3-[4-trans-[4-(4-Pyridyl)-piperazin-1-yl]carbonylamino]-cyclohexylpropionic acid, (c) 3-[4-trans-[4-(4-Pyridyl)-piperazin-1-yl]malonylamino]-cyclohexylcarboxylic acid, (d) 3-[4-[4-(4-Pyridyl)-piperazin-1-yl]carbonylamino]-piperidinopropionic acid, (e) [4-[4-(4-Pyridyl)-piperazin-1-yl]carbonylamino] piperidinoacetic acid, (f) Methyl [4-trans-[3-[4-(4-pyridyl)-piperazin-1-yl]-propionyl]-amino]cyclohexane carboxylate, (g) Methyl 3-[4-trans-[4-(4-pyridyl)-piperazin-1-yl]-carbonylamino]cyclohexyl propionate, (h) Methyl [4-trans-[4-(4-pyridyl)-piperazin-1-yl]-malonylamino]-cyclohexyl carboxylate, (i) Methyl 4-[[4-(4-pyridyl)-piperazin-1-yl]carbonylamino]-piperidino acetate, (j) Cyclohexyl [4-trans-[[4-(4-pyridyl)-piperazin-1-yl]-acetyl]-amino]-cyclohexane carboxylate, (k) Isobutyl [4-trans-[[4-(4-pyridyl)-piperazin-1-yl]acetyl]-amino]-cyclohexane carboxylate, the tautomers and the salts thereof.

According to the invention, the new compounds may be obtained, for example, by the following methods:

a. Reacting a compound of general formula $$R_a-N\underset{\phantom{xxx}}{\overgroup{\phantom{xxx}}}N-Y_1-OH \qquad (II)$$

wherein

R$_a$ and Y$_1$ are as hereinbefore defined, or the reactive derivatives thereof, with a compound of general formula $$H-Y_2'-Y_3-E' \qquad (III)$$

wherein

Y$_3$ is as hereinbefore defined,

Y$_2'$ has the meanings given for Y$_2$ hereinbefore, with the exception of the phenylene group, and E' denotes a C$_{1-6}$-alkoxy, phenyl-C$_{1-3}$-alkoxy or C$_{5-7}$-cycloalkoxy group.

The reaction of a carboxylic acid of general formula II, wherein Y$_1$ denotes an —A$_1$—CO— or —CO—A$_1$—CO— group is optionally carried out in a solvent or mixture of solvents such as methylene chloride, dimethylformamide, benzene, toluene, chlorobenzene, tetrahydrofuran, benzene/tetrahydrofuran or dioxan or in a corresponding amine of general formula III, optionally in the presence of a dehydrating agent, e.g. in the presence of isobutylchloroformate, tetraethylorthocarbonate, trimethylorthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methylmorpholine or triethylamine, conveniently at temperatures between 0° and 150° C., preferably at temperatures between 0° and 100° C.

The reaction of a corresponding reactive compound of general formula II such as the esters, imidazolides or halides thereof with an amine of general formula III is preferably carried out in a corresponding amine as solvent, optionally in the presence of another solvent such as methylene chloride or ether and preferably in the presence of a tertiary organic base such as triethylamine, N-ethyldiisopropylamine or N-methyl-morpholine at temperatures between 0° and 150° C., preferably at temperatures between 50° and 100° C.

b. In order to prepare a compound of general formula I, wherein at least one of the groups R$_2$ or E must contain a reactive hydrogen atom, with the proviso that E has the meanings given for E hereinbefore with the exception of the R$_5$—CO—O—(R$_3$CR$_4$)—O— group:

converting a compound of general formula

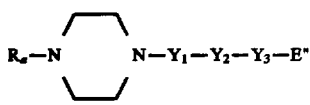 (IV)

wherein $R_a$ and $Y_1$ to $Y_3$ are as hereinbefore defined and E" denotes a hydroxy group or together with the adjacent carbonyl group of the group $Y_3$ denotes a group which may be converted into a carboxyl group by hydrolysis, treatment with an acid or base, thermolysis or hydrogenolysis, but at least one of the groups $NR_2$ or E" must contain a cleavable group, into a compound of general formula I, wherein at least one of the groups $R_2$ or E must contain a reactive hydrogen atom, with the proviso that E has the meanings given for E hereinbefore, with the exception of the $R_5$—CO—O—$(R_3CR_4)$—O— group.

As protective groups for a hydroxy group of a carboxy group, for example, the functional derivatives of a carboxy group such as the unsubstituted or substituted amides, esters, thioesters, trimethylsilylesters, orthoesters or iminoesters may be converted by hydrolysis into a carboxyl group, esters with tertiary alcohols, e.g. the tert.butyl ester, may be converted into a carboxy group by treatment with an acid or thermolysis and esters with aralkanols, e.g. the benzyl ester, may be converted into a carboxy group by hydrogenolysis.

The hydrolysis is appropriately carried out either in the presence of an acid such as hydrochloric acid, sulphuric acid, phosphoric acid, acetic acid, trichloroacetic acid, trifluoroacetic acid or mixtures thereof, or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxan, at temperatures between −10° C. and 120° C., e.g. at temperatures between ambient temperature and the boiling temperature of the reaction mixture.

Under the reaction conditions mentioned above, any N-acylamino or $C_{1-5}$-alkoxycarbonyl groups present such as an N-trifluoroacetylamino or tert.butyloxycarbonyl group may be converted into the corresponding amino groups.

If E" in a compound of formula IV denotes, for example, a tert.butyloxycarbonyl group, the tert.butyl group may also be cleaved by treating with an acid such as trifluoroacetic acid, formic acid, p-toluenesulphonic acid, sulphuric acid, hydrochloric acid, phosphoric acid or polyphosphoric acid, optionally in an inert solvent such as methylene chloride, chloroform, benzene, toluene, diethylether, tetrahydrofuran or dioxan, preferably at temperatures between −10° C. and 120° C., e.g. at temperatures between 0° and 60° C., or thermally, optionally in an inert solvent such as methylene chloride, chloroform, benzene, toluene, tetrahydrofuran or dioxan and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 120° C. Under the reaction conditions mentioned above, any N-tert.butyloxycarbonylamino groups present may be converted into the corresponding amino groups.

If E" in a compound of formula IV denotes, for example, a benzyloxycarbonyl group, the benzyl group may also be hydrogenolytically cleaved in the presence of a hydrogenation catalyst such as palladium/charcoal, in a suitable solvent such as methanol, ethanol, ethanol/water, glacial acetic acid, ethyl acetate, dioxan or dimethylformamide, preferably at temperatures between 0° and 50° C., e.g. at ambient temperature, under a hydrogen pressure of 1 to 5 bar. During hydrogenolysis, other groups may also be reduced at the same time, e.g. a nitro group may be reduced to an amino group or a benzyloxy group to a hydroxy group, or an N-benzylamino, N-benzylimino, N-benzyloxycarbonylamino or N-benzyloxycarbonylimino group to a corresponding amino or imino group.

c. In order to prepare a compound of general formula I, wherein $Y_2$ has the meanings given hereinbefore, with the exception of the phenylene group, and $Y_3$ denotes an —$A_2$—CO— group wherein $A_2$ denotes an n-$C_{2-4}$-alkenylene group optionally substituted by a $C_{1-5}$-alkyl, phenyl or phenyl-$C_{1-3}$-alkyl group:

reacting a compound of general formula

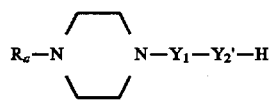 (V)

wherein $R_a$ and $Y_1$ are as hereinbefore defined and $Y_2'$ has the meanings given for $Y_2$ hereinbefore with the exception of the phenylene, 3-piperidinylene or 4-piperidinylene group, with a compound of general formula $A_2'$—CO—E  (VI)

wherein

E is as hereinbefore defined and $A_2'$ denotes an n-$C_{2-4}$-alkenylene group optionally substituted by a $C_{1-5}$-alkyl, phenyl or phenyl-$C_{1-3}$-alkyl group.

The reaction is preferably carried out in a solvent such as methanol, ethanol, methylene chloride, tetrahydrofuran, toluene, dioxan, dimethylsulphoxide or dimethylformamide, optionally in the presence of a tertiary organic base such as N-ethyl-diisopropylamine or N-methyl-morpholine at temperatures between −30° and 150° C., but preferably at temperatures between 0° and 100° C.

d. Reacting a compound of general formula

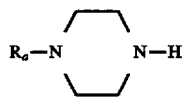 (VII)

wherein $R_a$ is as hereinbefore defined, with a compound of general formula $Z_1$—$Y_1$—$Y_2$—$Y_3$—E 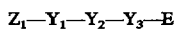 (VIII)

wherein $Y_1$, $Y_2$, $Y_3$ and E are as hereinbefore defined and $Z_1$ denotes a nucleophilic leaving group such as a halogen atom, a hydroxy or sulphonic acid ester group, e.g. a chlorine, bromine or iodine atom, a hydroxy, imidazolyl, 4-nitrophenyloxy, methanesulphonyloxy or p-toluenesulphonyloxy group, or, if $Y_1$ denotes a carbonyl group, $Z_1$ together with $R_1$ denotes another carbon-nitrogen bond.

The reaction is preferably carried out in a solvent such as methanol, ethanol, methylene chloride, tetrahydrofuran, toluene, dioxan, dimethylsulphoxide or dimethylformamide, optionally in the presence of an inorganic or tertiary organic base or optionally in the presence of a dehydrating agent at temperatures between −30° and 200° C.

With a compound of general formula VIII, wherein $Z_1$ denotes a nucleophilic leaving group, or with an isocyanate of general formula VIII, the reaction is preferably carried out in a solvent such as methylene chloride, acetonitrile, tetrahydrofuran, toluene, dimethylformamide or dimethylsulphoxide, optionally in the presence of a base such as sodium hydride, potassium carbonate, potassium tert.butoxide or N-ethyl-diisopropylamine or optionally in the presence of a dehydrating agent such as triphenylphosphine/diethylazodicarboxylate at temperatures between −20° and 100° C., preferably at temperatures between 0° and 60° C.

e. In order to prepare a compound of general formula I, wherein E denotes a $C_{1-6}$-alkoxy, phenyl-$C_{1-3}$-alkoxy, $C_{5-7}$-cycloalkoxy or $R_5$—CO—O—$(R_3CR_4)$—O— group:

reacting a compound of general formula $$R_a-N\begin{pmatrix}\phantom{x}\\\phantom{x}\end{pmatrix}N-Y_1-Y_2-Y_3-OH \qquad (IX)$$

wherein $R_a$ and $Y_1$ to $Y_3$ are as hereinbefore defined, with a compound of general formula $$HO-R_b \qquad (X)$$

or with a compound of general formula $$Z_2-R_c \qquad (XI)$$

wherein $R_b$ denotes a $C_{1-6}$-alkyl, phenyl-$C_{1-3}$-alkyl or $C_{5-7}$-cycloalkyl group, $R_c$ denotes a $C_{1-6}$-alkyl, phenyl-$C_{1-3}$-alkyl, $C_{5-7}$-cycloalkyl or $R_5$—CO—O—$(R_3CR_4)$ group, wherein $R_3$, $R_4$ and $R_5$ are as hereinbefore defined and $Z_2$ denotes a leaving group such as a halogen atom, e.g. a chlorine or bromine atom.

With an alcohol of general formula X, the reaction is conveniently carried out in a solvent or mixture of solvents such as methylene chloride, benzene, toluene, chlorobenzene, tetrahydrofuran, benzene/tetrahydrofuran or dioxan, but preferably in an alcohol of formula X, optionally in the presence of an acid such as hydrochloric acid or in the presence of a dehydrating agent, e.g. in the presence of isobutyl chloroformate, thionyl chloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole, N,N'-thionyldiimidazole or triphenylphosphine/carbon tetrachloride, optionally in the presence of a base such as potassium carbonate, N-ethyl-diisopropylamine or N,N-dimethylaminopyridine, appropriately at temperatures between 0° and 150° C., preferably at temperatures between 0° and 80° C.

With a compound of general formula XI the reaction is appropriately carried out in a solvent such as methylene chloride, tetrahydrofuran, dioxan, dimethylsulphoxide, dimethylformamide or acetone, optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may simultaneously serve as solvents, or optionally in the presence of silver carbonate or silver oxide at temperatures between −30° and 100° C., but preferably at temperatures between −10° and 80° C.

f. Reacting a compound of general formula $$R_a-N\begin{matrix}\diagup CH_2-CH_2-Z_3\\ \diagdown CH_2-CH_2-Z_4\end{matrix} \qquad (XII)$$

wherein $R_a$ is as hereinbefore defined, $Z_3$ and $Z_4$, which may be identical or different, denote nucleophilic leaving groups such as halogen atoms or sulphonyloxy groups, e.g. chlorine or bromine atoms, methanesulphonyloxy or p-toluenesulphonyloxy groups, with a compound of general formula $$NH_2-Y_1-Y_2-Y_3-E \qquad (XIII)$$

wherein

E, $Y_2$ and $Y_3$ are as hereinbefore defined and $Y_1$ denotes an —$A_1$—CO— or —$A_2$—$SO_2$— group, wherein $A_1$ and $A_2$ are as hereinbefore defined.

The reaction is conveniently carried out in a solvent such as methylene chloride, tetrahydrofuran, dioxan, dimethylsulphoxide, dimethylformamide or acetone, optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may simultaneously serve as solvents, or optionally in the presence of silver carbonate or silver oxide at temperatures between −30° and 100° C., but preferably at temperatures between −10° and 80° C.

In the reactions described hereinbefore, any reactive groups present such as hydroxy, carboxy, amino or imino groups may be protected during the reaction by means of conventional protecting groups which are removed by cleaving after the reaction.

For example, the protecting group for a carboxyl group may be a trimethylsilyl, methyl, ethyl, tert.butyl, benzyl or tetrahydropyranyl group, and the protecting group for an amino or imino group may be a formyl, acetyl, trifluoroacetyl, allyloxycarbonyl, ethoxycarbonyl, tert.-butoxycarbonyl, benzyloxycarbonyl, benzyl, methoxybenzyl or 2,4-dimethoxybenzyl group and for the amino group a phthalyl group may also be considered.

The optional subsequent cleaving of a protecting group may, for example, be carried out hydrolytically in an aqueous solvent, e.g. in water, isopropanol/water, acetic acid/water, tetrahydrofuran/water or dioxan/water, in the presence of an acid such as trifluoroacetic acid, hydrochloric acid or sulphuric acid or in the presence of an alkali metal base such as sodium hydroxide or potassium hydroxide or by ether cleaving, e.g. in the presence of iodotrimethylsilane, at temperatures between 0° and 120° C., preferably at temperatures between 10° and 100° C.

However, a benzyl, methoxybenzyl or benzyloxycarbonyl group may for example be cleaved hydrogenolytically, e.g. using hydrogen in the presence of a catalyst such as palladium/charcoal in a solvent such as methanol, ethanol, ethyl acetate or glacial acetic acid, optionally with the addition of an acid such as hydrochloric acid, at temperatures between 0° and 100° C., but preferably at temperatures between 20° and 60° C., under a hydrogen pressure of 1 to 7 bar, preferably 3 to 5 bar. However, a 2,4-dimethoxybenzyl group is preferably cleaved in trifluoroacetic acid in the presence of anisol.

A tert.butyl or tert.butyloxycarbonayl group is preferably cleaved by treatment with an acid such as trifluoroacetic acid or hydrochloric acid or by treatment with iodotrimethylsilane, optionally using a solvent such as methylene chloride, dioxan, methanol or ether.

A trifluoroacetyl group is preferably cleaved by treating with an acid such as hydrochloric acid, optionally in the presence of a solvent such as acetic acid at temperatures between 50° and 120° C. or by treating with sodium hydroxide solution or aqueous lithium hydroxide solution, optionally in the presence of a solvent such as tetrahydrofuran or methanol at temperatures between 0° and 50° C.

An allyloxycarbonyl group is cleaved by treating with a catalytic amount of tetrakis-(triphenylphosphine)-palladium (O), preferably in a solvent such as tetrahydrofuran and preferably in the presence of an allyl group acceptor such as morpholine or 1,3-dimedone, at temperatures between 0° and 100° C., preferably at ambient temperature and under inert gas, or by treating with a catalytic amount of tris-(triphenylphosphine)-rhodium(I)chloride, in a solvent such as aqueous ethanol and optionally in the presence of a base such as 1,4-diazabicyclo[2.2.2]octane, at temperatures between 20° and 70° C.

A phthalyl group is preferably cleaved in the presence of hydrazine or a primary amine such as methylamine, ethylamine or n-butylamine in a solvent such as methanol, ethanol, isopropanol, toluene/water or dioxan, at temperatures between 20° and 50° C.

Furthermore, the compounds of general formula I obtained may be resolved into their enantiomers and/or diastereomers as mentioned hereinbefore. Thus, for example, cis/trans mixtures may be resolved into their cis and trans isomers, and compounds having at least one optically active carbon atom may be resolved into their enantiomers.

Thus, for example, the cis/trans mixtures obtained may be resolved by chromatography into the cis and trans isomers thereof and the compounds of general formula I which occur in racemate form may be separated by methods known per se (see Allinger N. L. and Eliel E. L. in "Topics in Stereochemistry", Vol. 6, Wiley Interscience, 1971) into their optical antipodes, and compounds of general formula I having at least 2 stereogenic centres may be separated on the basis of their physical chemical differences using known methods, e.g. by chromatography and/or fractional crystallisation, into the diastereomers thereof, which, if they occur in racemic form, may subsequently be separated into the enantiomers as mentioned above.

The separation of enantiomers is preferably effected by column separation on chiral phases or by recrystallisation from an optically active solvent or by reacting with an optically active substance (especially acids and the activated derivatives thereof or alcohols), which forms salts or derivatives such as esters or amides with the racemic compound, and separation of the diasteromeric salt mixture or derivative thus obtained, e.g. on the basis of their different solubilities, whilst the free antipodes may be released from the pure diastereomeric salts by the action of suitable agents. Particularly useful, optically active acids include, for example, the D- and L-forms of tartaric acid, and dibenzoyltartaric acid, di-o-tolyl tartaric acid, malic acid, mandelic acid, camphorsulphonic acid, glutamic acid, aspartic acid and quinic acid. Examples of optically active alcohols include for example (+)- or (−)-menthol and examples of optically active acyl groups in amides include, for example, (+)- or (−)-menthyloxycarbonyl.

Moreover, the compounds of formula I obtained may be converted into the salts thereof, particularly for pharmaceutical use into the physiologically acceptable salts thereof with inorganic or organic acids. Examples of suitable acids include hydrochloric acid, hydrobromic acid, sulphuric acid, phosphoric acid, fumaric acid, succinic acid, lactic acid, citric acid, tartaric acid or maleic acid.

In addition, the new compounds of formula I thus obtained, if they contain a carboxyl group, may subsequently, if desired, be converted into the addition salts thereof with inorganic or organic bases, more particularly, for pharmaceutical use, into the physiologically acceptable addition salts thereof. Examples of suitable bases include sodium hydroxide, potassium hydroxide, arginine, cyclohexylamine, ethanolamine, diethanolamine and triethanolamine.

The compounds used as starting materials are known from the literature in some cases or may be obtained by methods known from the literature (see Examples I to XXXI).

As already mentioned, the new piperazine derivatives of general formula I and the addition salts thereof, particularly the physiologically acceptable addition salts thereof with inorganic or organic acids or bases, have valuable pharmacological properties, and in addition to having an inhibitory effect on inflammation and bone degradation, they have in particular antithrombotic, antiaggregatory and tumour- or metastasis-inhibiting effects.

By way of example, the compounds of general formula I were investigated for their biological effects as follows:

1. Inhibition of binding of $^3$H-BIBU 52 to human thrombocytes:

A suspension of human thrombocytes in plasma is incubated with $^3$H-BIBU 52 [=(3S,5S)-5-[(4'-amidino-4-biphenylyl)oxymethyl]-3-[(carboxyl)methyl]-2-pyrrolidinone[3-$^3$H-4-biphenylyl]] (see DE-A-4,214,245), which replaces the $^{125}$I fibrinogen ligand known from the literature, and various concentrations of the substance to be tested. The free and bound ligand is separated by centrifuging and quantified by scintillation counting. The inhibition of $^3$H-BIBU 52 binding by the test substance is determined from the measurements obtained.

In order to do this, donor blood is taken from an anticubital vein and anticoagulated with trisodium citrate (final concentration 13 mM). The blood is centrifuged for 10 minutes at 170×g and the supernatant platelet-rich plasma (PRP) is removed. The remaining blood is vigorously centrifuged once more in order to obtain plasma. The PRP is diluted 1:10 with autologous plasma. 750 μl are incubated with 50 μl of physiological saline solution, 100 μl of test substance solution, 50 μl of $^{14}$C-sucrose (3,700 Bq) and 50 μl of $^3$H-BIBU 52 (final concentration: 5 nM) at ambient temperature for 20 minutes. In order to measure the non-specific binding, 5 μl of BIBU 52 (final concentration: 30 μM) are used instead of the test substance. The samples are centrifuged for 20 seconds at 10,000×g and the supernatant is poured off. 100 μl thereof are counted in order to determine the amount of free ligand. The pellet is dissolved in 500 μl of 0.2N NaOH, 450 μl are mixed with 2 ml of scintillator and 25 μl of 5N HCl and measured. The residual plasma remaining in the pellet is determined from the $^{14}$C-content and the bound ligand is determined from the $^3$H-measurement. After the non-specific binding has been deducted, the pellet activity is plotted against the concentration of the test substance and the concentration for a 50% inhibition of binding is determined.

2. Antithrombotic activity

Method

The thrombocyte aggregation is measured using the method of Born and Cross (J. Physiol. 170: 397 (1964)) in platelet-rich plasma taken from healthy volunteers. To inhibit coagulation, the blood is mixed with 3.14% sodium citrate in a volume ratio of 1:10.

Collagen-induced aggregation

The pattern of the decrease in optical density of the platelet suspension is photometrically measured and recorded after the addition of the aggregation-triggering substance. The rate of aggregation is determined from the angle of inclination of the density curve. The point on the curve where there is maximum light transmittance is used to calculate the optical density.

The concentration of collagen used is as small as possible but sufficient to produce an irreversible reaction curve. Standard commercial collagen produced by Hormonchemie of Munich is used.

Before the addition of the collagen the plasma is incubated for 10 minutes with the substance at 37° C.

From the measurements obtained the $EC_{50}$ is determined, which indicates the concentration giving a 50% change in the optical density in terms of the inhibition of aggregation.

The following table shows the results which were obtained:

| Substance (Example No.) | Fibrinogen binding test $IC_{50}$ [nM] | Inhibition of platelet aggregation $EC_{50}$ [nM] |
| --- | --- | --- |
| 5 | 0.21 | 0.26 |
| 5(6) | 0.25 | 0.16 |
| 5(7) | 0.23 | 0.25 |
| 5(8) | 0.41 | 0.60 |
| 5(9) | 0.430 | 4.40 |
| 1 | >100 | 3.32 |
| 4 | 0.55 | 0.39 |
| 1(6) | 0.38 | 3.60 |
| 4(1) | 48 | >10 |

The new compounds are well tolerated because after intravenous administration of 30 mg/kg of the compounds of general formula I according to the invention to mice, no toxic side effects were observed.

In the light of their inhibitory effect on cell-cell or cell-matrix interactions, the new piperazine derivatives of general formula I and the physiologically acceptable salts thereof are suitable for combating or preventing diseases in which smaller or greater cell aggregates occur or in which cell-matrix interactions play a part, e.g. in treating or preventing venous and arterial thrombosis, cerebrovascular diseases, lung embolism, cardiac infarction, arteriosclerosis, osteoporosis and the metastasis of tumours and the treatment of genetically caused or acquired disorders of cell interactions with one another or with solid structures. They are also suitable for parallel therapy in thrombolysis with fibrinolytics or vascular interventions such as transluminal angioplasty or in the treatment of shock, psoriasis, diabetes and inflammation.

For treating or preventing the diseases mentioned above, the dosage is between 0.1 μg and 30 mg/kg of body weight, preferably 1 μg to 15 mg/kg of body weight, given in up to 4 doses per day. For this purpose the compounds of formula I produced according to the invention, optionally in conjunction with other active substances such as thromboxane receptor antagonists and thromboxane synthesis inhibitors or combinations thereof, serotonin antagonists, α-receptor antagonists, alkylnitrates such as glycerol trinitrate, phospho-diesterase inhibitors, prostacyclin and the analogues thereof, fibrinolytics such as tPA, prourokinase, urokinase, streptokinase, or anticoagulants such as heparin, dermatane sulphate, activated protein C, vitamin K antagonists, hirudine, inhibitors of thrombin or other activated clotting factors, may be incorporated together with one or more inert conventional carriers and/or diluents, e.g. corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof, into conventional galenic preparations such as plain or coated tablets, capsules, powders, suspensions, solutions, sprays or suppositories.

The Examples which follow are intended to illustrate the invention:

Preparation of the starting compounds:

EXAMPLE I

3-[4-(4-Pyridyl)-piperazin-1-yl]propionic acid a) Methyl 3-[4-(4-pyridyl)-piperazin-1-yl]propionate dihydrochloride A solution of 4 g (0.0245 Mol) of 1-(4-pyridyl)-piperazine, 21.1 g (0.245 Mol) of methyl acrylate and 6.5 ml (0.0358 Mol) of a 40% methanolic solution of benzyltrimethylammonium hydroxide in 50 ml of methanol and 50 ml of chloroform is refluxed for 3 hours. The solvent is then distilled off under a water jet vacuum and the residue is partitioned between methylene chloride and water. The methylene chloride extracts are dried over sodium sulphate and evaporated down. The residue is dissolved in ether and acidified to pH 3 with ethereal hydrochloric acid. The precipitated hydrochloride is suction filtered, washed with ether and dried in vacuo.

Yield: 6.4 g (81% of theory),

Melting point: >330° C.

$R_f$ value: 0.45 (silica gel; methylene chloride/methanol/conc. ammonia=9:1:0.25)

b) 3-[4-(4-Pyridyl)-piperazin-1-yl]-propionic acid

To a solution of 6 g (0.02 Mol) of methyl 3-[4(4-pyridyl) piperazin-1-yl]propionate dihydrochloride in 80 ml of tetrahydrofuran and 100 ml of water is added a solution of 4.2 g (0.1 Mol) of lithium hydroxide in 100 ml of water and the mixture is stirred for two hours at ambient temperature. It is then evaporated to dryness in vacuo and the residue remaining is taken up in absolute ethanol. 5.3 g (0.1 Mol) of ammonium chloride are added, the inorganic salts precipitated are suction filtered and the solution remaining is evaporated to dryness. The residue is triturated with ether and suction filtered.

Yield: 3.4 g (72.8% of theory),

Melting point: from 215° C.

$R_f$ value: 0.21 (silica gel; methylene chloride/methanol= 9:1)

EXAMPLE II

4-[4-(4-Pyridyl)-piperazin-1-yl]butyric acid dihydrochloride a) Ethyl 4-[4-(4-pyridyl)-piperazin-1-yl]butyratedihydrochloride To a solution of 6.4 g (0.039 Mol) of 1-(4-pyridyl)-piperazine in 150 ml of methanol are added, with stirring, 9.1 g (0.047 Mol) of ethyl 4-bromobutyrate (6.7 ml) and 6.0 g (0.047 Mol) of N-ethyl-diisopropylamine (4.3 ml) and the solution thus obtained is refluxed for 48 hours. The solution is then evaporated down in vacuo and the residue is partitioned between methylene chloride and water. The organic phase is dried over sodium sulphate and evaporated to dryness in vacuo. The residue remaining is dissolved in ethanol and acidified to pH 3 with ethereal hydrochloric acid. It is again evaporated to dryness in vacuo the residue is triturated with acetone and the crystals are suction filtered.

Yield: 6 g (43.7% of theory).

Mass spectrum: $M^+=277$ $R_f$ value: 0.60 (silica gel; methylene chloride/methanol/conc. ammonia=9:1:0.25)

b) 4-[4-(4-Pyridyl)-piperazin-1-yl]butyric acid 6 g (0.017 Mol) of ethyl 4-[4-(4-pyridyl)-piperazin-1-yl] butyrate dihydrochloride are dissolved in 120 ml of semiconcentrated hydrochloric acid. The solution is left to stand 18 hours at ambient temperature and then evaporated to dryness in vacuo. The residue remaining is triturated with acetone and the amorphous solid is suction filtered and dried.

Yield: 5.2 g (94.2% of theory),

Mass spectrum: $M^+=249$ $R_f$ value: 0.11 (silica gel; methylene chloride/methanol/conc. ammonia=4:1:0.2)

EXAMPLE III

[4-(4-Pyridyl)-piperazin-1-yl]acetic acid dihydrochloride a) Methyl [(4-(4-pyridyl)-piperazin-1-yl]acetic acid hydrochloride Prepared from 1-(4-pyridyl)-piperazine and methyl bromoacetate analogously to Example IIa.

b) [4-(4-Pyridyl)-piperazin-1-yl]acetic acid-dihydrochloride

Prepared from methyl [4-(4-pyridyl)-piperazin-1-yl]acetate dihydrochloride and semiconcentrated hydrochloric acid analogously to Example IIb.

EXAMPLE IV

5-[4-(4-Pyridyl)-piperazin-1-yl]valeric acid dihydrochloride a) Ethyl 5-[4-(4-pyridyl)-piperazin-1-yl]valerate To a solution of 6.4 g (0.039 Mol) of 1-(4-pyridyl)-piperazine in 150 ml of ethanol are added, with stirring, 11.5 g (0.055 Mol) ethyl 5-bromovalerate (8.7 ml) and 7.1 g (0.055 Mol) of N-ethyl-diisopropylamine (5.0 ml) and the solution thus obtained is refluxed for 48 hours. The solution is then evaporated down in vacuo and the residue is partitioned between methylene chloride and water. The organic phase is dried over sodium sulphate and evaporated to dryness in vacuo.

Yield: 10 g (87.5% of theory), Oil $R_f$ value: 0.60 (silica gel; methylene chloride/methanol/conc. ammonia=4:1:0.2)

b) 5-[4-(4-Pyridyl)-piperazin-1-yl]valeric acid-dihydrochloride 10 g (0.034 Mol) of ethyl 5-[4-(4-pyridyl)-piperazin-1-yl]valerate are dissolved in 150 ml of semiconcentrated hydrochloric acid. This solution is left to stand for 18 hours at ambient temperature and then evaporated to dryness in vacuo. Acetone is added twice and each time the mixture is evaporated to dryness in vacuo, to obtain a colourless foam which is further reacted as a crude product.

Yield: 9.0 g (78% of theory), $R_f$ value: 0.09 (silica gel; methylene chloride/methanol=4:1)

EXAMPLE V

[4-(4-Pyridyl)-piperazin-1-yl]malonic acid a) [4-(4-Pyridyl)-piperazin-1-yl]malonate A solution of 4.0 g (0.025 Mol) of 1-(4-pyridyl)-piperazine, 4.4 g (0.029 Mol) of ethyl malonate chloride (3.8 ml) and 3.9 g (0.029 Mol) of N-ethyl-diisopropylamine (5 ml) in 150 ml of dry tetrahydrofuran is refluxed for 6 hours. The solution is then evaporated to dryness in vacuo and the residue is purified over a silica gel column, using methylene chloride/methanol/conc. ammonia=9:0.5:0.05 and 9:1:0.1 as eluant.

Yield: 5 g (73.6% of theory),

Mass spectrum; $M^+=277$ $R_f$ value: 0.45 (silica gel; methylene chloride/methanol/conc. ammonia=9:1:0.1)

b) [4-(4-Pyridyl)-piperazin-1-yl]malonic acid

A solution of 5.0 g (0.018 Mol) of ethyl [4-(4-pyridyl)-piperazin-1-yl]malonate in 100 ml of semiconcentrated hydrochloric acid is left to stand overnight at ambient temperature and then evaporated to dryness in vacuo. The residue is combined three times with acetone and in each case evaporated to dryness in vacuo.

Yield: 4.7 g (89.5% of theory), Colourless foam

Mass spectrum; $M^+=249$ $R_f$ value: 0.10 (silica gel; methylene chloride/methanol/conc. ammonia=4:1:0.2)

EXAMPLE VI

[4-(4-Pyridyl)-piperazin-1-yl]carbonylamino] piperidine a) 4-[[4-(4-pyridyl)-piperazin-1-yl]carbonylamino]-N-benzyl-piperidine To a solution of 8.2 g (0.05 Mol) of N,N'-carbonyldiimidazole and 4.3 g (0.063 Mol) of imidazole in 300 ml of dry dimethylformamide is added, at −5° C. and with stirring, a solution of 8 g (0.042 Mol) of 4-amino-N-benzyl-piperidine (8.6 ml) in 20 ml of dry dimethylformamide and the mixture is stirred for a further hour at −5° C. and then for one hour at ambient temperature. Then 6.9 g (0.042 Mol) of 4-pyridyl-piperazine, dissolved in 50 ml of dimethylformamide, are added dropwise and the mixture is stirred overnight at ambient temperature. The solution is evaporated to dryness in vacuo and the residue is distributed between ethyl acetate and water. The combined organic extracts are dried, evaporated down and purified over a silica gel column, using methylene chloride/methanol/conc. ammonia=9:0.5:0.05 as eluant.

Yield: 5.0 g (31.2% of theory),

Mass spectrum; $M^+=379$ $R_f$ value: 0.45 (silica gel; methylene chloride/methanol/conc. ammonia=9:1:0.1)

b) 4-[[4-(4-Pyridyl)-piperazin-1-yl]carbonylamino]piperidine

A solution of 5 g (0.13 Mol) of 4-[[4-(4-pyridyl)-piperazin-1-yl]carbonylamino]-N-benzyl-piperidine in 100 ml of methanol is exhaustively hydrogenated at ambient temperature under a pressure of 50 psi over palladium dihydroxide on charcoal as catalyst. After the catalyst has been filtered off the remaining solution is evaporated to dryness in vacuo.

Yield: 2.0 g (54% of theory), Oil
Mass spectrum: M$^+$=289
R$_f$ value: 0.10 (silica gel; methylene chloride/methanol/conc. ammonia=9:1:0.1)

EXAMPLE VII

Methyl 4-amino-piperidin-1-yl-acetate dihydrochloride a) 4-tert.Butyloxycarbonylamino-N-benzyl-piperidine To a solution of 50 g (0.26 Mol) of 4-amino-1-benzyl-piperidine in 300 ml of dry dioxan is added, with stirring and cooling with water, a solution of 60 g (0.276 Mol) of di-tert.butyldicarbonate in 150 ml of dry dioxan. After it has all been added the mixture is stirred for 4 hours at ambient temperature and evaporated to dryness in vacuo. The residue remaining is triturated with a little ether and petroleum ether, suction filtered and washed with petroleum ether.

Yield: 70.6 g (92.6% of theory),
Melting point: 114°–115° C.
R$_f$ value: 0.60 (silica gel; methylene chloride/methanol=9:1)

b) 4-tert.Butyloxycarbonylamino-piperidine

A solution of 5 g (0.017 Mol) of 4-tert.butyloxycarbonylamino-N-benzyl-piperidine in 50 ml of methanol is acidified with ethereal hydrochloric acid to pH 6 and exhaustively hydrogenated over palladium on charcoal (10%) under a hydrogen pressure of 50 psi at ambient temperature. The catalyst is filtered off, the filtrate is evaporated to dryness in in vacuo, the residue is triturated with ether and the solids are suction filtered.

Yield: 3.3 g (95.7% of theory),
Mass spectrum: M$^+$=200
R$_f$ value: 0.13 (silica gel; methylene chloride/methanol=9:1)

c) Methyl 4-tert.butyloxycarbonylamino-piperidin-1-yl-acetate

A solution of 3.0 g (0.013 Mol) of 4-tert.butyloxycarbonyl-amino-piperidine, 1.9 g (0.13 Mol) of bromoacetate (1.2 ml) and 2.6 g (0.025 Mol) of triethylamine (3.4 ml) is stirred overnight at ambient temperature. It is then evaporated to dryness in vacuo and the residue is partitioned between ethyl acetate and water. The organic phase is dried over sodium sulphate and evaporated down.

Yield: 3.1 g (89.8% of theory),
Mass spectrum: M$^+$=272
R$_f$ value: 0.43 (silica gel; methylene chloride/methanol=9:1)

d) Methyl 4-aminopiperidin-1-yl-acetate dihydrochloride

A solution of 3.1 g (0.011 Mol) of methyl 4-tert.butyloxycarbonyl-amino-piperidino acetate in 30 ml of methanol is acidified with 30 ml of ethereal hydrochloric acid and left to stand overnight at ambient temperature. It is then evaporated down to dryness in in vacuo, the residue is triturated with ether and the solid is suction filtered.

Yield: 2.4 g (100% of theory),
Mass spectrum: M$^+$=140
R$_f$ value: 0.10 (silica gel; methylene chloride/methanol=9:1)

EXAMPLE VIII

Methyl N-[4-nitrophenyloxycarbonyl]-3-(4-piperidinyl)-propionate

To a solution of 4.75 g (0.0229 Mol) of methyl 3-(4-piperidinyl)-propionate and 4.93 g (0.0229 Mol) of p-nitrophenylchloroformate in 200 ml of dry tetrahydrofuran are added dropwise at 0° C., with stirring, 8 ml (0.0573 Mol) of triethylamine and the mixture is stirred overnight at ambient temperature. It is then heated to ambient temperature for 4 hours and evaporated to dryness in vacuo. The residue is partitioned between methylene chloride and water, the organic phase is separated off, dried and evaporated down. The residue remaining is purified over a silica gel column, using methylene chloride as eluant.

Yield: 9 g oil which contains 4-nitrophenol as an impurity.
Mass spectrum: M$^+$=336
R$_f$ value: 0.93 (silica gel; methylene chloride/methanol=9:1)

EXAMPLE IX

N-tert.Butyloxycarbonyl-N-[4-[[4-(4-pyridyl)-piperazin-1-yl]-carbonyl]piperidinyl]-β-alanine methyl ester To a solution of 5 g (0.0155 Mol) of N-tert.butyloxycarbonyl-N-(4-piperidinyl)-β-alanine methyl ester hydrochloride and 4.8 ml (0.0341 Mol) of triethylamine in 150 ml of dry tetrahydrofuran is added dropwise, at ambient temperature and with stirring, a solution of 4.1 g (0.0186 Mol) of p-nitrophenylchloroformate in 20 ml of dry tetrahydrofuran and the mixture is stirred for a further 4 hours at ambient temperature. The triethylammonium chloride precipitated is suction filtered. The remaining solution is combined with 2.53 g (0.0155 Mol) of 1-(4-pyridyl)-piperazine and 2.8 ml (0.0155 Mol) of N-ethyl-diisopropylamine and left to stand overnight at ambient temperature. After evaporation to dryness, the oily residue remaining is heated to 140° C. for 6 hours. Since thin layer chromatography shows that the reaction is not yet complete, a further 1 g (0.061 Mol) of N-ethyl-diisopropylamine is added and the mixture is heated to 140° C. for a further 6 hours. After cooling, it is triturated with petroleum ether, decanted off and the residue is partitioned between ethyl acetate and water. The ethyl acetate phase is washed with 1N sodium bicarbonate solution, dried and evaporated down. The residue is purified over a silica gel column, using methylene chloride with 2.5% methanol and methylene chloride with 5% methanol and 0.4% conc. ammonia as eluant.

Yield: 2.36 g (32% of theory),
Mass spectrum: (M+H)$^+$=476
R$_f$ value: 0.40 (silica gel; methylene chloride/methanol=9:1)

EXAMPLE X

Methyl N-(4-nitrophenyloxycarbonyl)-4-(4-piperidinyl)]-butyrate

Prepared from methyl 4-(4-piperidinyl)]-butyrate hydrochloride, p-nitrophenylchloroformate and N-ethyldiisopropylamine analogously to Example VIII.

Oil which slowly crystallises.

$R_f$ value: 0.11 (silica gel; methylene chloride/methanol= 9:1)

EXAMPLE XI

N-tert.Butyloxycarbonyl-N-[[4-[4-(4-pyridyl)-piperazin-1-yl]-carbonyl]piperidinyl]glycine methyl ester Prepared from N-tert.butyloxycarbonyl-N-[4-[1-(4-nitrophenyloxycarbonyl)-piperidinyl]]-glycine methyl ester (prepared analogously to Example VIII) and 1-(4-pyridyl)-piperazine analogously to Example IX.

EXAMPLE XII

N-tert.Butyloxycarbonyl-N-(4-piperidinyl)-β-alanine methyl ester-hydrochloride a) N-[1-Benzyl-4-piperidinyl]-β-alanine methyl ester hydrochloride A solution of 50 g (0.263 Mol) of 4-amino-1-benzyl-piperidine and 28.5 ml (0.263 Mol) of ethyl acrylate in 300 ml methanol is refluxed for 4 hours. It is then evaporated down to dryness in vacuo, the residue is dissolved in acetone, acidified to pH 3 with ethereal hydrochloric acid and evaporated to dryness in vacuo once more. The residue remaining is triturated with acetone. The crystalline product precipitated is suction filtered and dried.

Yield: 48.7 g (50.2% of theory),

Melting point: 172°–180° C. (Decomp.)

$R_f$ value: 0.60 (silica gel; methylene chloride/methanol= 9:1)

b) N-[1-Benzyl-4-piperidinyl]-N-tert.butyloxycarbonyl-β-alanine methyl ester hydrochloride A solution of 25 g (0.0716 Mol) of N-[1-benzyl-4-piperidinyl]-β-alanine methyl ester hydrochloride, 15.8 g (0.072 Mol) of di-tert.butyldicarbonate and 20 ml (0.138 Mol) of triethylamine in 100 ml dioxan and 100 ml water is left to stand at ambient temperature for 48 hours. The mixture is then evaporated to dryness in vacuo and the residue is partitioned between ethyl acetate and water. The organic phase is dried over sodium sulphate and evaporated down. The residue remaining is dissolved in ethanol and acidified to pH 6 with ethereal hydrochloric acid. The solution is evaporated to dryness in vacuo, the residue is stirred with acetone and the solid is suction filtered.

Yield: 24.1 g (81.5% of theory),

Melting point: 196°–197° C. (Decomp.)

$R_f$ value: 0,80 (silica gel; methylene chloride/methanol= 9:1)

c) N-tert.Butyloxycarbonyl-N-(4-piperidinyl)-β-alanine methyl ester hydrochloride 24 g (0.05 Mol) of N-[1-benzyl-4-piperidinyl]-N-tert.butyloxy-carbonyl-β-alanine methyl ester hydrochloride are exhaustively hydrogenated in 900 ml of methanol at ambient temperature under a hydrogen pressure of 50 psi over palladium on charcoal (10%) as catalyst. The catalyst is suction filtered and the solution is evaporated to dryness in vacuo.

Yield: 20.4 g Oil, $R_f$ value: 0.17 (silica gel; methylene chloride/methanol= 9:1)

EXAMPLE XIII

N-tert.Butyloxycarbonyl-N-(4-piperidinyl)-glycine methyl ester hydrochloride a) N-[1-Benzyl-4-piperidinyl]-glycine methyl ester dihydrochloride Prepared from 4-amino-1-benzyl-piperidine, methyl bromoacetate and N-ethyl-diisopropylamine.

b) N-[1-Benzyl-4-piperidinyl]-N-tert.butyloxycarbonyl-glycine methyl ester dihydrochloride Prepared from N-[1-benzyl-4-piperidinyl]-glycine methyl ester hydrochloride, di-tert.butyldicarbonate and triethylamine.

c) N-tert.Butyloxycarbonyl-N-(4-piperidinyl)-glycine methyl ester hydrochloride

Prepared from N-[1-benzyl-4-piperidinyl]glycine methyl ester hydrochloride by exhaustive hydrogenation over palladium on charcoal (10%).

EXAMPLE XIV

N-Methyl-N-(4-piperidinyl)-β-alanine methyl ester dihydrochloride a) N-[1-Benzyl-4-piperidinyl]-N-methyl-β-alanine methyl ester dihydrochloride A suspension of 28.8 g (0.026 Mol) of N-[1-benzyl-4-piperidinyl]-β-alanine methyl ester dihydrochloride, 2.7 g (0.09 Mol) of paraformaldehyde and 5.2 g (0.083 Mol) of sodium cyanoborohydride in 100 ml ethanol is stirred at ambient temperature for 24 hours. It is then diluted with water and acidified with iN hydrochloric acid to pH2. The mixture is extracted with ethyl acetate, the aqueous phase is made alkaline with dilute sodium hydroxide solution and exhaustively extracted with methylene chloride. The combined methylene chloride phases are dried and evaporated to dryness in vacuo. The residue is purified over a silica gel column, using methylene chloride with 3% and with 5% methanol as eluant. The combined eluates are acidified to $pH_3$ with ethereal hydrochloric acid and evaporated to dryness in vacuo. The residue is combined with acetone and suction filtered.

Yield: 20.8 g (69.5% of theory)

Melting point: 224°–227° C.

$R_f$ value: 0.60 (silica gel; methylene chloride/methanol= 4:1)

b) N-Methyl-N-(4-piperidinyl)-β-alanine methyl ester dihydrochloride

Prepared by hydrogenation of N-[1-benzyl-4-piperidinyl]-N-methyl-β-alanine methyl ester dihydrochloride with palladium on charcoal (10%).

Yield: 15.8 g (95.4% of theory)

Melting point: 194°–195° C. (Decomp.)

$R_f$ value: 0.09 (silica gel; methylene chloride/methanol= 9:1)

The following compounds may be prepared analogously to Example XIV:

(1) N-Methyl-N-(4-piperidinyl)-glycine methyl ester dihydrochloride a) N-[1-Benzyl-4-piperidinyl]-N-methyl-glycine methyl ester dihydrochloride Prepared from N-[1-benzyl-4-piperidinyl]glycine methyl ester dihydrochloride, paraformaldehyde and sodium cyanoborohydride.

b) N-Methyl-N-(4-piperidinyl)-glycine methyl ester dihydrochloride

Prepared from N-[1-benzyl-4-piperidinyl]-N-methyl-glycine methyl ester dihydrochloride by exhaustive hydrogenation over palladium on charcoal (10%).

(2) N-(2-Phenylethyl)-N-(4-piperidinyl)-β-alanine methyl ester dihydrochloride a) N-[1-Benzyl-4-piperidinyl]-N-(2-phenylethyl)-β-alanine methyl ester dihydrochloride Prepared from N-[1-benzyl-4-piperidinyl]-β-alanine methyl ester dihydrochloride, phenylacetaldehyde and sodium cyanoborohydride.

b) N-(2-Phenylethyl)-N-4-(piperidinyl)-β-alanine methyl ester dihydrochloride

Prepared from N-[1-benzyl-4-piperidinyl]-N-(2-phenylethyl)-β-alanine methyl ester dihydrochloride by exhaustive hydrogenation over palladium on charcoal (10%).

EXAMPLE XV

N-Acetyl-N-(4-piperidinyl)-β-alanine methyl ester hydrochloride a) N-Acetyl-N-[1-benzyl-4-piperidinyl]-β-alanine methyl ester hydrochloride A solution of 25 g (0.0716 Mol) of N-(1-benzyl-4-piperidinyl)-β-alanine methyl ester hydrochloride, 20 ml (0.143 Mol) of triethylamine and 8.1 ml (0.0859 Mol) of acetic anhydride in 300 ml of methanol is left to stand overnight at ambient temperature and then evaporated down in vacuo. The residue is dissolved in water, adjusted to pH 8 with 2N sodium hydroxide solution and extracted exhaustively with ethyl acetate. The combined ethyl acetate extracts are dried and evaporated to dryness in vacuo. The residue is purified over a silica gel column with methylene chloride containing 3% methanol. The eluates are evaporated down, the residue is dissolved in acetone, acidified to pH 6 with ethereal hydrochloric acid and concentrated by evaporation. The residue is crystallised using acetone/ether.

Yield: 19 g (74.7% of theory),

Melting point: 138°–140° C. (Decomp.)

$R_f$ value: 0.50 (silica gel; methylene chloride/methanol= 9:1)

b) N-Acetyl-N-(4-piperidinyl)-β-alanine methyl ester hydrochloride

Prepared analogously to Example XIIc by hydrogenation with palladium on charcoal (10%).

Yield: 13.2 g (93.2% of theory),
Highly hygroscopic solid
Mass spectrum: $M^+$=228

$R_f$ value: 0.09 (silica gel; methylene chloride/methanol= 9:1)

EXAMPLE XVI

Methyl 4-(4-piperidinyl)-butyrate hydrochloride a) Diethyl 2-[2-(4-pyridyl)-ethyl]malonate hydrochloride 13.4 g (0.583 Mol) of sodium are dissolved in 180 ml of absolute ethanol and 204 ml (1.35 Mol) of diethylmalonate are added in batches to the resulting solution, whereupon a colourless precipitate is formed. This precipitate is dissolved by heating to 30°–40° C. and diluting with absolute ethanol and a solution of 63 ml (0.583 Mol) of 4-vinylpyridine in 120 ml of absolute ethanol is added dropwise thereto within 1.5 hours with stirring. After it has all been added, the resulting mixture is refluxed for 3 hours, then concentrated down to a small volume and diluted with 450 ml of semi-concentrated hydrochloric acid. It is extracted twice with ether to remove excess diethylmalonate, the aqueous phase is made alkaline with sodium carbonate and extracted exhaustively with methylene chloride. The combined organic phases are dried and evaporated down. The residue is purified over a silica gel column using ethyl acetate/cyclohexane=1:1 as eluant. The oily residue (78.6 g=50.8% of theory) is dissolved in acetone and acidified to pH 3.5 with ethereal hydrochloric acid and evaporated down. The residue crystallises overnight, is triturated with acetone/ether and suction filtered.

Yield: 65 g (37% of theory), $R_f$ value: 0.80 (silica gel; methylene chloride/methanol= 9:1)

b) Diethyl 2-[2-(4-piperidinyl)-ethyl]malonate hydrochloride 64.5 g (0.21 Mol) of diethyl 2-[2-(4-pyridyl)-ethyl] malonate hydrochloride are hydrogenated exhaustively in 400 ml of absolute ethanol at ambient temperature under a hydrogen pressure of 50 psi over platinum dioxide as catalyst. After the catalyst has been removed by suction filtering, the solution remaining is evaporated to dryness in vacuo. The residue is crystallised with acetone and suction filtered.

Yield: 62.8 g (95.5% of theory) of highly hygroscopic crystals which liquefy in the air.

$R_f$ value: 0.22 (silica gel; methylene chloride/methanol= 9:1)

c) 4-(4-Piperidinyl)-butyric acid hydrochloride

A solution of 62 g (0.201 Mol) of diethyl 2-[2-(4-piperidinyl)-ethyl]-malonate hydrochloride in 600 ml of concentrated hydrochloric acid is refluxed for 24 hours and then evaporated to dryness in vacuo. The residue is mixed with toluene and evaporated down. This operation is repeated three times.

Yield: 44.3 g colourless crystals which still contain some toluene $R_f$ value: 0.19 (silica gel; methylene chloride/methanol= 9:1)

c) Methyl 4-(4-piperidinyl)-butyrate hydrochloride 18 ml (0.242 Mol) of thionyl chloride are slowly added dropwise to 800 ml of methanol with stirring at −10° C. then, at the same temperature, a solution of 44.3 g(0.201 Mol) of 4-(4-piperidinyl)-butyric acid hydrochloride in 100 ml of methanol is added dropwise, the resulting mixture is stirred overnight at ambient temperature and then evaporated to dryness in vacuo. The residue is partitioned between 50% potassium carbonate solution and ether. The aqueous phase is extracted twice more with ether. The combined ether extracts are dried and evaporated down. The residue is dissolved in methanol, acidified to pH 6 with ethereal hydrochloric acid and evaporated to dryness in vacuo. The residue remaining is triturated with acetone. The crystals precipitated are suction filtered.

Yield: 35.5 g (88.7% of theory)

Melting point: 99°–105° C. (Decomp.)

EXAMPLE XVII

Methyl 4-piperidinyloxy-acetate hydrochloride a) Methyl N-tert.butyloxycarbonyl-4-piperidinyloxy-acetate To a solution of 10 g (0.05 Mol) of N-tert.butyloxycarbonyl-4-piperidinol in 100 ml of dry tetrahydrofuran are added, with stirring 2.3 g (0.05 Mol) of sodium hydride (50% in oil) and stirring is continued for a further 2 hours. Then 7.6 g (0.05 Mol) of methyl bromoacetate (5 ml) are added dropwise with continued stirring and the mixture is stirred overnight.

The unreacted sodium hydride is destroyed by the addition of water. Extraction is carried out with ethyl acetate, the combined ethyl acetate extracts are dried and evaporated to dryness in vacuo. The residue is purified over a silica gel column (eluant: methylene chloride which contains 1% methanol).

Yield: 4.9 g (36.1% of theory),

Mass spectrum: M$^+$=273

R$_f$ value: 0.50 (silica gel; methylene chloride/methanol= 9.5:0.5)

b) Methyl 4-piperidinyloxy-acetate hydrochloride

A solution of 4.9 g (0.018 Mol) of methyl N-tert.butyloxycarbonyl-4-piperidinyloxyacetate in 10 ml of methanol is combined with 30 ml of ethereal hydrochloric acid and left to stand for 4 hours at ambient temperature. It is then evaporated to dryness in vacuo, the residue is combined with ether and the solids are suction filtered.

Yield: 3.1 g of colourless solids (82.5% of theory),

Mass spectrum: M$^+$=173

R$_f$ value: 0.10 (silica gel; methylene chloride/methanol= 9:1)

EXAMPLE XVIII

α-Bromo-4-methoxycarbonylmethyloxy-acetophenone a) 4-Methoxycarbonylmethyloxy-acetophenone To a solution of 8 g (0.06 Mol) of 4-hydroxy-acetophenone in 100 ml of dry dimethylformamide are added 9 g (0.06 Mol) of methyl bromoacetate (5.6 ml) and 8 g (0.06 Mol) of potassium carbonate. The mixture is refluxed for 5 hours and then stirred overnight at ambient temperature. The solution is evaporated to dryness in vacuo and the residue is partitioned between ethyl acetate and water. The combined organic extracts are dried and evaporated to dryness in vacuo. The residue is triturated with ether, suction filtered and dried.

Yield: 8.6 g of amorphous solid (70.3% of theory),

Mass spectrum: M$^+$=208

R$_f$ value: 0.45 (silica gel; ethyl acetate/cyclohexane=1:1)

b) α-Bromo-4-methoxycarbonylmethyloxy-acetophenone

To a solution of 2 g (0.0096 Mol) of 4-methoxycarbonylmethyloxy-acetophenone in 40 ml of ether and 10 ml of dioxan is added dropwise, with stirring and at ambient temperature, a suspension of 0.0106 Mol of bromodioxan (prepared from 1.7 g of bromine and 8 ml of dioxan) in dioxan. After the addition is complete it is stirred for a further 2 hours at ambient temperature and then evaporated to dryness in vacuo.

Yield: 1.3 g crude product,

R$_f$ value: 0.60 double spot (silica gel; ethyl acetate/cyclohexane=1:1)

The following compound may be prepared analogously to Example XVIII:

(1) Methyl 4-[α-bromo-acetyl]-phenylacetate

Prepared from methyl 4-acetyl-phenylacetate and bromodioxan.

EXAMPLE XIX

3-Methoxycarbonylmethyloxy-aniline a) 3Methoxycarbonylmethyloxy-nitrobenzene

To a solution of 9 g (0.065 Mol) of m-nitrophenol in 100 ml of dry dimethylformamide are added 8.8 g (0.065 Mol) of potassium carbonate and the mixture is stirred for ½ hour at ambient temperature. Then 10.9 g (0.07 Mol) of methyl bromoacetate (6.7 ml) are added and the mixture is heated to 80° C. for 5 hours. The solution is then evaporated to dryness in vacuo and the residue is partitioned between ethyl acetate and water. The combined organic phases are dried and evaporated to dryness in vacuo. The residue is triturated with ether, suction filtered and dried.

Yield: 9.2 g (67.3% of theory),

R$_f$ value: 0.55 (silica gel; methylene chloride)

b) 3-Methoxycarbonylmethyloxy-aniline 9.2 g (0.046 Mol) of 3-methoxycarbonylmethoxy-nitrobenzene are exhaustive hydrogenated in methanol over 1.5 g of Raney nickel under a hydrogen pressure of 50 psi and at ambient temperature. After the catalyst has been removed by suction filtering the solution is evaporated down.

Yield: 7.0 g Oil (88.7% of theory),

R$_f$ value: 0.50 (silica gel; ethyl acetate/cyclohexane=1:1)

EXAMPLE XX

4-Methyloxycarbonylmethyloxy-aniline a) 4-Methoxycarbonylmethyloxy-nitrobenzene

Prepared from 4-nitrophenol, methylbromoacetate and caesium carbonate analogously to Example XIXa.

Yield: 10.4 g (91.2% of theory),

Melting point: 86°–88° C.

b) 4-Methoxycarbonylmethyloxy-aniline

Prepared from 4-methoxycarbonylmethyloxy-nitrobenzene by hydrogenation over Raney nickel analogously to Example XIXb.

Yield: 9.5 g resin (98.4% of theory),

R$_f$ value: 0.60 (silica gel; methylene chloride/methanol= 9:1)

EXAMPLE XXI

Methyl 3-(4-amino-phenyl)-propionate hydrochloride

A solution of 15 g (0.0991 Mol) of 3-(4-amino-phenyl)-propionic acid in 100 ml methanol is combined dropwise with 12.96 g (0.11 Mol) of thionyl chloride (7.93 ml) with stirring and cooling with methanol/ice. After it has all been added, the mixture is stirred for a further 30 minutes and then overnight at ambient temperature. It is then evaporated to dryness in vacuo and the residue is crystallised from methanol/ether.

Yield: 16.8 g (85.6% of theory),

Melting point: 165°–167° C.

EXAMPLE XXII

N-[[4-(4-Pyridyl)-piperazin-1-yl]carbonyl]piperidin-4-carboxylic acid a) Methyl N-[[4-(4-pyridyl)-piperazin-1-yl]carbonyl]piperidin-4-carboxylate Prepared by reacting methyl piperidin-4-carboxylate with p-nitrophenyl-chloroformate in the presence of triethylamine to obtain methyl N-(4-nitrophenyloxycarbonyl)-piperidin-4-carboxylate and subsequently reacting this intermediate product with 1-(4-pyridyl)-piperazine analogously to Example IX.

b) N-[[4-(4-Pyridyl)-piperazin-1-yl]carbonyl]piperidin-4-carboxylic acid

Prepared by reacting methyl N-[[4-[4-pyridyl)-piperazin-1-yl]carbonyl]piperidin-4-carboxylate with semiconcentrated hydrochloric acid analogously Example 4.

EXAMPLE XXIII 4-(Ethoxycarbonyl-2-ethyloxy)-piperidine trifluoroacetate a) 4-(Ethoxycarbonyl-2-ethyloxy)-N-tert.butyloxycarbonylpiperidine 0.3 g (0.0027 Mol) of potassium-tert.butylate are added to a solution of 10 g (0.0497 Mol) of N-tert.butyloxycarbonyl-4-piperidinol in 20 ml of dioxan and then 13.5 ml (0.124 Mol) of ethyl acrylate are added dropwise, with stirring, and the mixture is refluxed for 7 hours. After stirring overnight at ambient temperature the mixture is evaporated to dryness in vacuo and the residue is partitioned between ethyl acetate and water. The organic phase is dried and evaporated to dryness in vacuo. The residue is purified over a silica gel column (eluant: cyclohexane/ethyl acetate=10:3).

Yield: 4.5 g of oil (30% of theory), $R_f$ value: 0.80 (silica gel; methylene chloride/methanol= 9:1)

b) 4-(Ethoxycarbonyl-2-ethyloxy)-piperidine trifluoroacetate 4.5 g (0.015 Mol) of 4-(ethoxycarbonyl-2-ethyloxy)-N-tert.butyloxycarbonyl-piperidine are left to stand for 4 hours in a mixture of 30 ml of methylene chloride and 20 ml of trifluoroacetic acid at ambient temperature. The mixture is evaporated to dryness in vacuo and 4.5 g of a colourless oil are obtained.

$R_f$ value: 0.20 (silica gel; methylene chloride/methanol= 9:1)

EXAMPLE XXIV

Methyl 4-trans-(L-alanyl)-amino-cyclohexane-carboxylate trifluoroacetate a) Methyl 4-trans-(N-tert.butyloxycarbonyl-L-alanyl)-amino- cyclohexane-carboxylate To a solution of 2.5 g (0.013 Mol) of (N-tert.butyloxycarbonyl-L-alanine and 3.9 ml (0.028 Mol) of triethylamine in 100 ml of dry dimethylformamide are added 1.8 ml (0.0145 Mol) of isobutylchloroformate at −50° C., with stirring, and the mixture is stirred for a further hour at ambient temperature. Then 2.6 g (0.013 Mol) of 4-amino-cyclohexane-carboxylate hydrochloride are added and the mixture is left to stand overnight. After evaporation and partitioning of the residue between water and ethyl acetate, the organic phase is dried and again evaporated to dryness. The residue is crystallised from ether/petroleum ether.

Yield: 3.47 g (80% of theory),

Melting point: 136°–137° C.

$R_f$ value: 0.60 (silica gel; methylene chloride/methanol 9:1)

b) Methyl 4-trans-(L-alanyl)-amino-cyclohexane-carboxylate trifluoroacetate

Prepared from 3.4 g (0.01 Mol) of 4-trans-(N-tert.butyloxy-carbonyl-L-alanyl)-amino-cyclohexane-carboxylate and 50% trifluoroacetic acid in methylene chloride analogously to Example XXIIIb.

Yield: 6 g of oily crude product, $R_f$ value: 0.28 (silica gel; methylene chloride/methanol= 9:1)

EXAMPLE XXV

Methyl N-(O-methyl-L-tyrosyl)-4-piperidinyloxy-acetate trifluoroacetate a) Methyl N-(tert.butyloxycarbonyl-O-methyl-L-tyrosyl)-4-piperidinyloxy-acetate Prepared from N-tert.butyloxycarbonyl-O-methyl-L-tyrosine, methyl 4-piperidinyloxy-acetate hydrochloride, isobutylchloroformate and triethylamine analogously to Example XXIVa.

b) Methyl N-(O-methyl-L-tyrosyl)-4-piperidinyloxy-acetate trifluoroacetate

Prepared from methyl N-(tert.butyloxycarbonyl)-O-methyl-L-tyrosyl)-4-piperidinyloxy-acetate and 50% trifluoroacetic acid in methylene chloride analogously to Example XXIIIb.

EXAMPLE XXVI

Methyl N-(L-alanyl-4-piperidinyloxy-acetate trifluoroacetate a) Methyl N-(tert.butyloxycarbonyl-L-alanyl-4-piperidinyloxy-acetate Prepared from N-tert.butyloxy-L-alanine, methyl 4-piperidinyloxy-acetate hydrochloride, isobutylchloroformate and triethylamine analogously to Example XXIVa.

b) Methyl N-(L-alanyl)-4-piperidinyloxy-acetate trifluoroacetate

Prepared from methyl N-(tert.butyloxycarbonyl-L-alanyl)-4-piperidinyloxy-acetate and 50% trifluoroacetic acid in methylene chloride analogously to Example XXIIIb.

EXAMPLE XXVII

Methyl 4-trans-(O-methyl-L-tyrosyl)-amino-cyclohexane-carboxylate trifluoroacetate a) Methyl 4-trans-(N-tert.butyloxycarbonyl-O-methyl-L-tyrosyl)-amino-cyclohexane-carboxylate Prepared from N-tert.butyloxycarbonyl-O-methyl-L-tyrosine, methyl 4-amino-cyclohexane-carboxylate hydrochloride, isobutylchloroformate and triethylamine analogously to Example XXIVa.

Melting point: 151°–153° C.

$R_f$ value: 0.7 (silica gel; methylene chloride/methanol= 9:1)

b) Methyl 4-trans-(O-methyl-L-tyrosyl)-amino-cyclohexane-carboxylate trifluoroacetate Prepared from methyl 4-trans-(N-tert.butyloxycarbonyl-O-methyl-L-tyrosyl)-amino-cyclohexane-carboxylate and 50% trifluoroacetic acid in methylene chloride analogously to Example XXIIIb.

$R_f$ value: 0.4 (silica gel; methylene chloride/methanol= 9:1)

EXAMPLE XXVIII

4-Methoxycarbonylmethyloxy-phenylacetic acid a) Benzyl 4-methoxycarbonylmethyloxy-phenyl-acetate To a suspension of 8.4 g (0.035 Mol) of benzyl 4-hydroxyphenylacetate and 4.8 g (0.035 Mol) of dried potassium carbonate in 100 ml of dimethylformamide are added slowly, after 45 minutes stirring at ambient temperature, 5.3 g (0.038 Mol) of methylbromoacetate and the mixture is then heated to 80° C. for 5 minutes whilst stirring continues. It is then stirred overnight at ambient temperature. The solid matter is filtered off and the mother liquor is evaporated to dryness under reduced pressure. The residue is purified over a silica gel column, using methylene chloride as eluant. Yield: 7.9 g amorphous solid (72.9% of theory).

b) 4-Methoxycarbonylmethyloxy-phenylacetic acid 7.8 g (0.025 Mol) of benzyl 4-methoxycarbonylmethyloxyphenylacetate are exhaustively hydrogenated in 150 ml of methanol in the presence of 8 g of palladium hydroxide on charcoal at ambient temperature and under a hydrogen pressure of 50 psi. After the removal of the catalyst the mother liquor is evaporated to dryness under reduced pressure.

Yield: 4.7 g of resinous crude product (84.5% of theory).

EXAMPLE XXIX

3-[[4-Methoxycarbonylmethyl)-piperidinyl] propionic acid hydrochloride a) Tert.butyl 3-[[4-methoxycarbonylmethyl)-piperidinyl]-propionate Prepared from methyl 4-piperidinyl-acetate hydrochloride, tert.butyl acrylate and Triton B analogously to Example 7.

b) 3-[[4-Methoxycarbonylmethyl)-piperidinyl]propionic acid hydrochloride

Prepared from tert.butyl 3-[(4-methoxycarbonylmethyl) piperidinyl]propionate and 50% trifluoroacetic acid in methylene chloride analogously to Example XXIIIb.

EXAMPLE XXX

3-[4-(4-Pyridyl)-piperazin-1-yl]propionic acid a) Ethyl 3-[4-[4-(4-pyridyl)-piperazin-1-yl]propionate Prepared from (4-pyridyl)-piperazine and ethyl acrylate analogously to Example 7.

$R_f$ value: 0.40 (silica gel; methylene chloride/methanol= 9:1)

b) 3-[4-[4-(4-Pyridyl)-piperazin-1-yl]propionic acid

Prepared from the compound of Example XXXa by hydrolysis in the presence of hydrogen chloride/water=1:1 analogously to Example 5.

$R_f$ value: 0.45 (silica gel; methylene chloride/methanol/ conc. ammonia=4:1:0.25)

EXAMPLE XXXI 4-((4-Pyridyl)-piperazin-1-yl)oxalic acid a) Methyl 4-((4-pyridyl)-piperazin-1-yl)oxalate Prepared from equimolar amounts of 4-(4-pyridyl)-piperazine, triethylamine and methyl oxalate chloride in tetrahydrofuran.

b) 4-((4-Pyridyl)-piperazin-1-yl)oxalic acid

Prepared from methyl 4-((4-pyridyl)-piperazin-1-yl) oxalate by hydrolysis with an equimolar amount of aqueous 1N sodium hydroxide solution in tetrahydrofuran at ambient temperature.

Preparation of the end products:

Example 1

Methyl[4-trans-[3-[4-(4-pyridyl)-piperazin-1-yl] propionyl]-amino]cyclohexane carboxylate To a solution of 1.2 g (0.0051 Mol) of 3-[4-(4-pyridyl)-piperazin-1-yl]propionic acid in 100 ml of dry dimethylformamide are added, with stirring and at ambient temperature, 1.8 g (0.0056 Mol) of 2-(1H-benzotriazol-1-yl)-1,1,3,3-tetramethyluronium-tetrafluoroborate, 0.8 g (0.0056 Mol) of 1-hydroxy-1H-benzotriazole, 1 g (0.0051 Mol) of methyl p-trans-amino-cyclohexylcarboxylate hydrochloride and 1 g (0.01 Mol) of N-methyl-morpholine and the mixture is stirred at ambient temperature for a further 24 hours. It is then evaporated to dryness in vacuo. The residue remaining is purified by chromatography over silica gel (eluant: methylene chloride/methanol/conc. ammonia=20:1:0.25).

Yield: 1.1 g (57.6% of theory),

Melting point: 162°–164° C.

$R_f$ value: 0.43 (silica gel; methylene chloride/methanol/ conc. ammonia=9:1:0.25)

The following compounds may be prepared analogously to Example 1:

(1) Methyl N-[3-[4-(4-pyridyl)-piperazin-1-yl]propionyl]-3-(4-piperidinyl)-propionate dihydrochloride Prepared from 3-[4-(4-pyridyl)-piperazin-1-yl]propionic acid and methyl 3-(4-piperidinyl)-propionate.

Amorphous solid.

Mass spectrum: $M^+$=388

$R_f$ value: 0.70 (silica gel; methylene chloride/methanol/ conc. ammonia=4:1:0.2)

(2) Methyl N-[4-[4-(4-pyridyl)-piperazin-1-yl]butyryl]-4-piperidinyl-acetate dihydrochloride Prepared from 4-[4-(4-pyridyl)-piperazin-1-yl]butyric acid dihydrochloride and methyl 4-piperidinyl-acetate hydrochloride Amorphous.

Mass spectrum: $M^+$=388

$R_f$ value: 0.70 (silica gel; methylene chloride/methanol/ conc. ammonia=4:1:0.2)

(3) Methyl[4-trans-[4-(4-pyridyl)-piperazin-1-yl] butyrylamino]cyclohexane-carboxylate dihydrochloride Prepared from 4-[4-(4-pyridyl)-piperazin-1-yl]butyric acid dihydrochloride and methyl p-trans-amino-cyclohexane-carboxylate hydrochloride.

Mass spectrum: $M^+$=388

$R_f$ value: 0.70 (silica gel; methylene chloride/methanol/ conc. ammonia=4:1:0.2)

(4) Methyl N-[5-[4-(4-pyridyl)-piperazin-1-yl]valeryl]-4-piperidinyl-acetate dihydrochloride Prepared from 5-[4-(4-pyridyl)-piperazin-1-yl]valeric acid dihydrochloride and methyl 4-piperidinyl-acetate hydrochloride.

Amorphous solid.

Mass spectrum: $M^+$=402

$R_f$ value: 0.75 (silica gel; methylene chloride/methanol/ conc. ammonia=4:1:0.2)

(5) Methyl[4-trans-[5-(4-pyridyl)-piperazin-1-yl]-valerylamino]cyclohexane-carboxylate-dihydrochloride Prepared from 5-[4-(4-pyridyl)-piperazin-1-yl]valeric acid dihydrochloride and methyl p-trans-amino-cyclohexane-carboxylate hydrochloride.

Amorphous solid.

Mass spectrum: $M^+$=402

$R_f$ value: 0.75 (silica gel; methylene chloride/methanol/ conc. ammonia=4:1:0.2)

(6) Methyl[4-trans-[4-(4-pyridyl)-piperazin-1-yl] malonylamino]cyclohexylcarboxylate hydrochloride Prepared from 4-[(4-pyridyl)-piperazin-1-yl]malonic acid hydrochloride and ethyl p-trans-amino-cyclohexane-carboxylate.

Amorphous solid.

Mass spectrum: $M^+$=402

$R_f$ value: 0.50 (silica gel; methylene chloride/methanol/ conc. ammonia=9:1:0.1)

(7) Methyl[N-[4-(4-Pyridyl)-piperazin-1-yl]-acetyl]-piperazino-acetate trihydrochloride Prepared from [4-(4-pyridyl)-piperazin-1-yl]acetic acid and methyl piperazino-acetate dihydrochloride.

Melting point: 122°–123° C.

Mass spectrum: $M^+=361$ $R_f$ value: 0.42 (silica gel; methylene chloride/methanol/conc ammonia=9:1:0.1)

(8) Methyl[4-trans-[[4-(4-pyridyl)-piperazin-1-yl]-acetyl]amino]cyclohexane-carboxylate dihydrochloride Prepared from [4-(4-pyridyl)-piperazin-1-yl]acetic acid and methyl 4-trans-amino-cyclohexane-carboxylate hydrochloride.

Melting point: 310°–313° C.

Mass spectrum: $M^+=360$ $R_f$ value: 0.45 (silica gel; methylene chloride/methanol= 9:1)

(9) 1-[[4-(4-Pyridyl)-piperazin-1-yl]carbonyl]-[(piperidin-4-yl)carbonyl]glycine-methyl ester hydrochloride Prepared from N-[[4-(4-pyridyl)-piperazin-1-yl]carbonyl]-piperazin-4-carboxylic acid and glycine methyl ester hydrochloride.

(10) Methyl N-[[4-(4-pyridyl)-piperazin-1-yl]acetyl]-4-(4-piperidinyl)-butyrate dihydrochloride Prepared from [4-(4-pyridyl)-piperazin-1-yl]acetic acid and methyl 4-(4-piperidinyl)-butyrate.

Foam

Mass spectrum: $M^+=388$ $R_f$ value: 0.48 (silica gel; methylene chloride/methanol= 9:1)

(11) Methyl[4-trans-[[4-(4-pyridyl)-piperazin-1-yl]-acetyl]methylamino]-cyclohexane-carboxylate dihydrochloride Prepared from [4-(4-pyridyl)-piperazin-1-yl]acetic acid and methyl 4-trans-methylamino-cyclohexane-carboxylate hydrochloride

(12) N-[[4-(4-Pyridyl)-piperazin-1-yl]-carbonylethyl]-4-(methylpiperidinyl-acetate)hydrochloride Prepared from 1-(4-pyridyl)-piperazine and 3-[(4-methoxycarbonylmethyl)-piperidinyl]propionic acid hydrochloride.

$R_f$ value: 0.21 (silica gel; methylene chloride/methanol/conc. ammonia=9:1:0.1)

Mass spectrum: $M^+=374$

(13) N-[[4-(4-Pyridyl)-piperazin-1-yl]-malonyl]-4-(methylpiperidinyl-acetate)hydrochloride Prepared from 4-[(4-pyridyl)-piperazin-1-yl]-malonic acid and methyl 4-piperidinyl-acetate hydrochloride.

$R_f$ value: 0.48 (silica gel; methylene chloride/methanol/conc. ammonia=9:1:0.1)

Mass spectrum: $M^+=394$

(14) Methyl[4-trans-[(4-Pyridyl)-piperazin-1-yl]-oxalylamino]-cyclohexane-carboxylate Prepared from 4-[(4-pyridyl)-piperazin-1-yl]oxalic acid and methyl trans-4-aminocyclohexane-carboxylate hydrochloride.

(15) Methyl N-[[4-(4-pyridyl)-piperazin-1-yl]-oxalyl]-4-piperidinyl-acetate

Prepared from 4-[(4-pyridyl)-piperazin-1-yl]oxalic acid and methyl 4-piperidinyl-acetate hydrochloride.

(16) Methyl N-[[4-(4-pyridyl)-piperazin-1-yl]-ethylcarbonyl]-4-piperidinyl-acetate hydrochloride Prepared from 3-[4-(4-pyridyl)-piperazin-1-yl]propionate and methyl 4-piperidinyl-acetate hydrochloride.

$R_f$ value: 0.38 (silica gel; methylene chloride/methanol/conc. ammonia=9:1:0.1)

Mass spectrum: $M^+=374$

Example 2

Methyl N-[3-[4-(4-pyridyl)-piperazin-1-yl]propionyl]-4-piperidinyl-acetate dihydrochloride To a solution of 0.3 g (0.0013 Mol) of 3-[4-(4-pyridyl)-piperazin-1-yl]propionic acid in 30 ml of dry dimethylformamide are added, with stirring, and at ambient temperature, 0.26 g (0.0013 Mol) of N,N'-dicyclohexylcarbodiimide, 0.2 g (0.0013 Mol) of 1-hydroxy-1H-benzotriazole and 0.25 g (0.0013 Mol) of methyl 4-piperidino-acetate and the resulting mixture is stirred for a further 24 hours at ambient temperature. It is then evaporated to dryness in vacuo. The residue remaining is purified by chromatography over silica gel (eluant:methylene chloride, containing 6%, 8% and 10% methanol). The residue remaining after evaporation is dissolved in methanol. This solution is acidified to pH 3 with ethereal hydrochloric acid and evaporated to dryness in vacuo.

Yield: 0.6 g (37.7% of theory), amorphous solid $R_f$ value: 0.48 (silica gel; methylene chloride/methanol= 4:1)

Example 3

Methyl[4-[3-[4-(4-pyridyl)-piperazin-1-yl]propionyl]-amino]phenylacetate dihydrochloride A solution of 3.1 g (0.01 Mol) of 3-[4-(4-pyridyl)-piperazin-1-yl]propionic acid, 1.8 g (0.011 Mol) of N,N'-carbonyldiimidazole, 3 g (0.03 Mol) of N-methylmorpholine and 2 g (0.01 Mol) of methyl 4-aminophenylacetate in 200 ml of dry dimethylformamide is left to stand overnight at ambient temperature and then evaporated to dryness in vacuo. The residue remaining is purified by chromatography over silica gel (eluant:methylene chloride/methanol/conc. ammonia= 9:1:0.1). After evaporation of the eluates the residue remaining is dissolved in methanol and acidified to pH 3 with ethereal hydrochloric acid. It is again evaporated to dryness in vacuo and an amorphous colourless solid is obtained.

Yield: 1.0 g (22% of theory),

Mass spectrum: $M^+=382$ $R_f$ value: 0.75 (silica gel; methylene chloride/methanol/conc. ammonia=4:1:0.2)

Example 4

Methyl 3-[4-trans-[4-(4-pyridyl)-piperazin-1-yl]-carbonylamino]cyclohexylpropionate To a solution of 1.2 g (0.007 Mol) of N,N'-carbonyldiimidazole and 0.6 g (0.0092 Mol) of imidazole in 50 ml of dry tetrahydrofuran are added at 0° C., with stirring, a suspension of 1.4 g (0.0061 Mol) of methyl p-trans-aminocyclohexylpropionate and then 0.8 g (0.0061 Mol) of N-ethyldiisopropylamine. After it has all been added the mixture is stirred for half an hour at +5° C. and then a solution of 1 g (0.0061 Mol) of 4-pyridylpiperazine in 30 ml of dry tetrahydrofuran is added dropwise. After it has all been added the mixture is stirred overnight at ambient temperature. The solution is evaporated to dryness in vacuo and the residue remaining is partitioned between ethyl acetate and water. The combined ethyl acetate phases are dried and evaporated down. The residue is purified by chromatography over a silica gel column (eluant: methylene chloride/methanol/conc. ammonia=9:1:0.1).

Yield: 0.5 g (21.8% of theory),

Melting point: 64°–66° C.

Mass spectrum: $M^+=374$ $R_f$ value: 0.7 (silica gel; methylene chloride/methanol/conc. ammonia=4:1:0.2)

The following compounds may be prepared analogously to Example 4:

(1) Methyl 4-[[4-(4-pyridyl)-piperazin-1-yl]carbonyl-amino]-piperidino-acetate

Prepared from 4-pyridyl-piperazine, methyl 4-amino-piperidino-acetate, imidazole and N,N'-carbonyldiimidazole.

Melting point: 143°–144° C.
Mass spectrum: M⁺=361
$R_f$ value: 0.45 (silica gel; methylene chloride/methanol/ conc. ammonia=9:1:0.1)

(2) Methyl[3-[[4-(4-pyridyl)-piperazin-1-yl]carbonyl-amino]-phenoxy]-acetate

Prepared from 1-(4-pyridyl)-piperazine and 3-methoxycarbonylmethyloxy-aniline with 1,1'-carbonyldi-(1,2,4-triazole).

Melting point: 180°–182° C.
Mass spectrum: M⁺=370
$R_f$ value: 0.37 (silica gel; methylene chloride/methanol/ conc. ammonia=9:1:0.1)

Example 5

[4-trans-[3-[4-(4-Pyridyl)-piperazin-1-yl]propionyl] amino]-cyclohexane-carboxylic acid dihydrochloride A solution of 0.4 g (0.0011 Mol) of methyl [4-trans-[3-[4-(4-pyridyl)-piperazin-1-yl]propionyl]amino] cyclohexane-carboxylate in 40 ml of semiconcentrated hydrochloric acid is stirred overnight at ambient temperature and then evaporated to dryness in vacuo. The residue remaining is triturated with acetone, the solid matter is filtered off, washed with acetone and dried.

Yield: 0.35 g (90.9% of theory),

Melting point: 252°–254° C.

$R_f$ value: 0.24 (silica gel; methylene chloride/methanol/ conc. ammonia=4:1:0.25)

The following compounds may be prepared analogously to Example 5:

(1) N-[3-[4-(4-Pyridyl)-piperazin-1-yl]propionyl]-4-piperidinyl-acetic acid dihydrochloride Prepared from methyl N-[3-[4-(4-pyridyl)-piperazino] propionyl]-4-piperidinyl-acetate dihydrochloride Melting point: 218°–220° C.

$R_f$ value: 0.27 (silica gel; methylene chloride/methanol= 4:1)

(2) N-[3-[4-(4-Pyridyl)-piperazin-1-yl]propionyl]-3-(4-piperidinyl)-propionic acid Prepared from methyl N-[3-[4-(4-pyridyl)-piperazin-1-yl] propionyl]-3-(4-piperidinyl)-propionate dihydrochloride Amorphous solid.
Mass spectrum: M⁺=374
$R_f$ value: 0.22 (silica gel; methylene chloride/methanol/ conc. ammonia=4:1:0.2)

(3) N-[4-[4-(4-Pyridyl)-piperazin-1-yl]butyryl]-4-piperidinyl-acetic acid dihydrochloride Prepared from ethyl N-[4-[4-(4-pyridyl)-piperazin-1-yl]-butyryl]-4-piperidinyl-acetate dihydrochloride Amorphous solid.
Mass spectrum: (M+H)⁺=375
$R_f$ value: 0.13 (silica gel; methylene chloride/methanol/ conc. ammonia=4:1:0.2)

(4) [4-trans-[4-[4-(4-Pyridyl)-piperazin-1-yl]butyryl]amino] cyclohexane-carboxylic acid dihydrochloride Prepared from methyl[4-trans-[4-[4-(4-pyridyl)-piperazin-1-yl]-butyryl]amino]cyclohexane-carboxylate dihydrochloride.

Amorphous solid.
Mass spectrum: (M+H)⁺=375
$R_f$ value: 0.19 (silica gel; methylene chloride/methanol/ conc. ammonia=4:1:0.2)

(5) [4-trans-[5-[4-(4-Pyridyl)-piperazin-1-yl]valeryl]-amino]-cyclohexane-carboxylic acid dihydrochloride Prepared from methyl [4-trans-[5-[4-(4-pyridyl)-piperazin-1-yl]valeryl]amino]cyclohexane-carboxylate dihydrochloride.

Mass spectrum: M⁺=388
$R_f$ value: 0.18 (silica gel; methylene chloride/methanol/ conc. ammonia=4:1:0.2)

(6) 3-[4-trans-[4-(4-Pyridyl)-piperazin-1-yl]carbonylamino] cyclohexylpropionic acid hydrochloride Prepared from methyl 3-[4-trans-[4-(4-pyridyl)-piperazin-1-yl]-carbonylamino]cyclohexylpropionate.

Melting point: 140°–142° C.
Mass spectrum: M⁺=360
$R_f$ value: 0.10 (silica gel; methylene chloride/methanol/ conc. ammonia=4:1:0.2)

(7) [4-trans-[4-(4-Pyridyl)-piperazin-1-yl]malonylamino] cyclohexylcarboxylic acid hydrochloride Prepared from ethyl[4-trans-[4-(4-pyridyl)-piperazin-1-yl]malonylamino]cyclohexyl-carboxylate hydrochloride.

Melting point: 203°–205° C.
Mass spectrum: M⁺=360
$R_f$ value: 0.10 (silica gel; methylene chloride/methanol/ conc. ammonia=9:1:0.1)

(8) 3-[4-[4-(4-pyridyl)-piperazin-1-yl]carbonylamino] piperidinopropionic acid dihydrochloride Prepared from methyl 3-[4-[4-(4-pyridyl)-piperazin-1-yl] carbonylamino]piperidino-propionate.

Melting point: 235°–236° C.
Mass spectrum: M⁺=361
$R_f$ value: 0.11 (silica gel; methylene chloride/methanol/ conc. ammonia=4:1:0.2)

(9) [4-[4-(4-Pyridyl)-piperazin-1-yl]carbonylamino] piperidino-acetic acid

Prepared from methyl[4-[4-(4-pyridyl)-piperazin-1-yl] carbonylamino]piperidino-acetate.

Melting point: 210°–212° C.
Mass Spectrum: M⁺=347
$R_f$ value: 0.10 (silica gel; methylene chloride/methanol/ conc. ammonia=4:1:0.2)

(10) N-[[4-(4-pyridyl)-piperazin-1-yl]carbonyl]-3-(4-piperidinyl)-propionic acid hydrochloride Prepared from methyl N-[[4-(pyridyl)-piperazin-1-yl] carbonyl]-3-(4-piperidinyl)-propionate hydrochloride.

Melting point: 171°–178° C.
$R_f$ value: 0.47 (Reversed Phase Plate RP18; methanol/ sodium chloride solution (5%)=6:4)

(11) N-[4-[[4-(4-pyridyl)-piperazin-1-yl]carbonyl] piperidinyl]-β-alanine dihydrochloride Prepared from N-[4-[[4-(pyridyl)-piperazin-1-yl] carbonyl]piperidinyl]-β-alanine-methyl ester dihydrochloride.

Melting point: 234°–237° C.
$R_f$ value: 0.75 (Reversed Phase Plate RP18; methanol/5% sodium chloride solution=6:4)

(12) N-Methyl-N-[4-[[4-(4-pyridyl)-piperazin-1-yl] carbonyl]piperidinyl]-β-alanine dihydrochloride Prepared from N-methyl-N-[4-[[4-(4-pyridyl)-piperazin-1-yl]carbonyl]piperidinyl]-β-alanine methyl ester.

(13) N-Acetyl-N-[4-[[4-(4-pyridyl)-piperazin-1-yl] carbonyl]piperidinyl]-β-alanine hydrochloride Prepared from N-acetyl-N-[4-[[4-(4-pyridyl)-piperazin-1-yl]carbonyl]piperidinyl]-β-alanine methyl ester hydrochloride.

(14) N-[4-[[4-(4-Pyridyl)-piperazin-1-yl]carbonyl] piperidinyl]glycine dihydrochloride Prepared from N-[4-[[4-(4-pyridyl)-piperazin-1-yl] carbonyl]piperidinyl]glycine methyl ester dihydrochloride.

(15) N-Methyl-N-[4-[[4-(4-pyridyl)-piperazin-1-yl] carbonyl]piperidinyl]glycine dihydrochloride Prepared from N-methyl-N-[4-[[4-(4-pyridyl)-piperazin-1-yl]carbonyl]piperidinyl]glycine methyl ester dihydrochloride.

(16) N-Acetyl-N-[4-[[4-(4-pyridyl)-piperazin-1-yl] carbonyl]piperidinyl]glycine hydrochloride Prepared from N-acetyl-N-[4-[[4-(4-pyridyl)-piperazin-1-yl]carbonyl]piperidinyl]glycine methyl ester hydrochloride.

(17) N-(2-Phenylethyl)-N-[4-[[4-(4-pyridyl)-piperazin-1-yl] carbonyl]piperidinyl]-β-alanine dihydrochloride Prepared from N-(2-phenylethyl)-N-[4-[[4-(4-pyridyl)-piperazin-1-yl]carbonyl]piperidinyl]-β-alanine methyl ester.

(18) N-[[4-(4-Pyridyl)-piperazin-1-yl]carbonyl]-4-(4-piperidinyl)-butyric acid hydrochloride Prepared from methyl N-[[4-(4-pyridyl)-piperazin-1-yl] carbonyl]-4-(4-piperidinyl)-butyrate hydrochloride.

Melting point: 147°–149° C. (Decomp.)

$R_f$ value: 0.29 (Reversed Phase Plate RP18; methanol/5% sodium chloride solution=6:4)

(19) N-[[4-(4-pyridyl)-piperazin-1-yl]acetyl] piperazinoacetic acid trihydrochloride Prepared from methyl N-[[4-(4-pyridyl)-piperazin-1-yl] acetyl]piperazinoacetate trihydrochloride.

(20) [4-trans-[[4-(4-Pyridyl)-piperazin-1-yl]acetyl]amino] cyclohexane-carboxylic acid dihydrochloride Prepared from methyl [4-trans-[[4-(4-pyridyl)-piperazin-1-yl]acetyl]amino]cyclohexane-carboxylate dihydrochloride.

Melting point: 298°–300° C. (Decomp.)

Mass spectrum: $M^+=346$ $R_f$ value: 0.70 (Reversed Phase Plate RP18; methanol/5% sodium chloride solution=6:4)

(21) [3-[[4-(4-Pyridyl)-piperazin-1-yl]carbonylamino] phenoxy]acetic acid hydrochloride Prepared from methyl[3-[[4-(4-pyridyl)-piperazin-1-yl] carbonylamino]phenoxy]acetate.

Melting point: 225°–228° C.

Mass spectrum: $M^+=356$ $R_f$ value: 0.60 (silica gel; methylene chloride/methanol/ conc. ammonia=2:1:0.25)

(22) 4-[[4-(4-Pyridyl)-piperazin-1-yl]acetyl]phenylacetic acid dihydrochloride

Prepared from methyl 4-[[4-(4-pyridyl)-piperazin-1-yl] acetyl]phenyl-acetate dihydrochloride.

(23) 3-[4-[4-(4-Pyridyl)-piperazin-1-yl]carbonylamino] phenyl]propionic acid hydrochloride Prepared from methyl 3-[4-[4-(4-pyridyl)-piperazin-1-yl] carbonylamino]phenyl]propionate hydrochloride.

(24) N-[4-trans-[4-(4-Pyridyl)-piperazin-1-yl] carbonylamino]cyclohexyl]glycine dihydrochloride Prepared from N-[4-trans-[4-(4-pyridyl)-piperazin-1-yl] carbonylamino]cyclohexyl]glycine methyl ester dihydrochloride.

(25) N-[4-trans-[4-(4-pyridyl)-piperazin-1-yl] carbonylaminocyclohexyl]sarcosine dihydrochloride Prepared from N-[4-trans-[4-(4-pyridyl)-piperazin-1-yl] carbonylamino]cyclohexyl]sarcosine methyl ester dihydrochloride.

(26) N-Acetyl-N-[4-trans-[4-(4-pyridyl)-piperazin-1-yl] carbonylaminocyclohexyl]glycine hydrochloride Prepared from N-acetyl-N-[4-trans-[4-(4-pyridyl)-piperazin-1-yl]carbonylaminocyclohexyl]glycine methyl ester hydrochloride.

(27) N-[4-[4-(4-Pyridyl)-piperazin-1-yl] carbonylaminophenyl]glycine hydrochloride Prepared from N-[4-[4-(4-pyridyl)-piperazin-1-yl] carbonylaminophenyl]glycine methyl ester hydrochloride.

(28) N-[4-[4-(4-Pyridyl)-piperazin-1-yl] carbonylaminophenyl]sarcosine hydrochloride Prepared from N-[4-[4-(4-pyridyl)-piperazin-1-yl] carbonylaminophenyl]sarcosine methyl ester hydrochloride.

(29) N-Acetyl-N-[4-[4-(4-pyridyl)-piperazin-1-yl] carbonylaminophenyl]glycine hydrochloride Prepared from N-acetyl-N-[4-[4-(4-pyridyl)-piperazin-1-yl]carbonylaminophenyl]glycine methyl ester hydrochloride.

(30) N-[[4-(4-Pyridyl)-piperazin-1-yl]carbonyl]-3-(piperidin-4-yloxy)-propionic acid hydrochloride Prepared from ethyl N-[[4-(4-pyridyl)-piperazin-1-yl] carbonyl]-3-(piperidin-4-yloxy)-propionate hydrochloride.

Melting point: 118°–122° C. (Decomp.)

(31) [4-trans-[[4-(4-Pyridyl)-piperazin-1-yl]carbonylamino] cyclohexyloxy]acetic acid hydrochloride Prepared from methyl [4-trans-[[4-(4-pyridyl)-piperazin-1-yl]carbonylamino]cyclohexyloxy]acetate hydrochloride.

(32) N-[[4-(4-pyridyl)-piperazin-1-yl]-carbonyl]-(piperidin-4-yloxy-acetic acid hydrochloride Prepared from methyl N-[[4-(4-pyridyl)-piperazin-1-yl] carbonyl]-(piperidin-4-yloxy)-acetate hydrochloride.

(33) N-[[4-(4-Pyridyl)-piperazin-1-yl]-carbonyl](piperidin-4-yl.)-carbonyl]glycine hydrochloride Prepared from N-[[4-(4-pyridyl)-piperazin-1-yl]carbonyl] (piperidin-4-yl)-carbonyl]glycine methyl ester hydrochloride.

(34) N-[[4-(4-Pyridyl)-piperazin-1-yl]acetyl]-4-(4-piperidin-4-yl)-butyric acid dihydrochloride Prepared from methyl N-[[4-(4-pyridyl)-piperazin-1-yl] acetyl]-4-(4-piperidinyl)-butyrate dihydrochloride.

Melting point: 109°–112° C.

Mass spectrum: $M^+=374$ $R_f$ value: 0.60 (Reversed Phase Plate RP18; methanol/5% sodium chloride solution=6:4)

(35) [4-trans-[[4-(4-Pyridyl)-piperazin-1-yl]acetyl] methylamino]-cyclohexane-carboxylic acid dihydrochloride Prepared from methyl[4-trans-[[4-(4-pyridyl)-piperazin-1-yl]acetyl]methylamino]cyclohexane-carboxylate dihydrochloride

(36) [4-trans-[2S-[4-(4-Pyridyl)-piperazin-1-yl]-propionyl] amino]cyclohexane-carboxylic acid dihydrochloride Prepared from methyl [4-trans-[2S-[4-(4-pyridyl)-piperazin-1-yl]propionyl]amino]cyclohexane-carboxylate dihydrochloride

(37) [4-trans-[2S-[4-(4-Pyridyl)-piperazin-1-yl]-(3-(4-methoxyphenyl)-propionyl)]amino]cyclohexane-carboxylic acid dihydrochloride Prepared from methyl [4-trans-[2S-[4-(4-pyridyl)-piperazin-1-yl]-(3-(4-methoxyphenyl)-propionyl)]amino] cyclohexanecarboxylate dihydrochloride.

(38) N-[2S-[4-(4-pyridyl)-piperazin-1-yl]-propionyl] piperidin-4-yloxy)-acetic acid dihydrochloride Prepared from methyl N-[2S-[4-(4-pyridyl)-piperazin-1-yl]propionyl]-(piperidin-4-yloxy)-acetate dihydrochloride.

(39) N-[2S-[4-(4-Pyridyl)-piperazin-1-yl]-(3-(4-methoxyphenyl)-propionyl)]piperidin-4-yloxy)-acetic acid dihydrochloride Prepared from methyl N-[2S-[4-(4-pyridyl)-piperazin-1-yl]-(3-(4-methoxyphenyl)-propionyl)]-(piperidin-4-yloxy)-acetate dihydrochloride.

(40) N-[[4-(4-Pyridyl)-piperazin-1-yl]-carbonylethyl]-4-piperidinyl-acetic acid hydrochloride Prepared from methyl N-[[4-(4-pyridyl)-piperazin-1-yl]carbonylethyl]-4-piperidinyl-acetate hydrochloride.

R$_f$ value: 0.095 (silica gel; methylene chloride/methanol/conc. ammonia=2:1:0.25)

Mass spectrum: (M+H)$^+$=361

(41) N-[[4-(4-Pyridyl)-piperazin-1-yl]ethylcarbonyl]-4-piperidinyl-acetic acid hydrochloride Prepared from methyl N-[[4-(4-pyridyl)-piperazin-1-yl]ethylcarbonyl]-4-piperidinyl-acetate hydrochloride.

R$_f$ value: 0.5 (Reversed Phase Plate RP18; methanol/5%= NaCl solution=3:2)

Mass spectrum: M$^+$=360

(42) N-[[4-(4-Pyridyl)-piperazin-1-yl]malonyl]-4-(piperidinylacetic acid)hydrochloride Prepared from methyl N-[[4-(4-pyridyl)-piperazin-1-yl]malonyl]-4-piperidinyl-acetate hydrochloride.

Mass spectrum: M$^+$=374

(43) [4-trans-[(4-Pyridyl)-piperazin-1-yl]oxalylamino]cyclohexane-carboxylic acid hydrochloride Prepared from methyl [4-trans-[(4-pyridyl)-piperazin-1-yl]oxalylamino]cyclohexane-carboxylate and equimolar amounts of sodium hydroxide.

(44) N-[[4-(4-Pyridyl)-piperazin-1-yl]-oxalyl]-4-piperidinylacetic acid

Prepared from methyl N-[[4-(4-pyridyl)-piperazin-1-yl]-oxalyl]-4-piperidinyl-acetate and equimolar amounts of sodium hydroxide.

Example 6

4-[3-[4-(4-Pyridyl)-piperazin-1-yl]propionylamino]phenylacetic acid

A solution of 0.6 g (0.0013 Mol) of methyl 4-[3-[4-(4-pyridyl)piperazin-1-yl]propionylamino]phenylacetate-dihydrochloride in 10 ml of tetrahydrofuran is combined with 10 ml of 1N sodium hydroxide solution and stirred overnight. It is then neutralised with 2N hydrochloric acid and evaporated to dryness in vacuo. The residue remaining is extracted twice with absolute ethanol. The combined ethanol extracts are evaporated to dryness in vacuo. The residue is extracted with methylene chloride/methanol=1:1, the combined extracts are evaporated to dryness and the residue is triturated with ether. The amorphous solid precipitated is suction filtered and dried.

Yield: 0.46 g (94.8% of theory),

Mass spectrum: (M+H)$^+$=369

R$_f$ value: 0.68 (silica gel; methylene chloride/methanol/conc. ammonia=2:1:0.2)

The following compound is prepared analogously to Example 6:

(1) N-[5-[4-(4-Pyridyl)-piperazin-1-yl]valeryl]-4-piperidinylacetic acid

Prepared from methyl N-[5-[4-(4-pyridyl)-piperazin-1-yl]valeryl]-4-piperidinyl-acetate and 1N sodium hydroxide solution.

Amorphous solid.

Mass spectrum: M$^+$=388

R$_f$ value: 0.28 (silica gel; methylene chloride/methanol/conc. ammonia=4:1:0.2)

Example 7

Methyl 3-[4-[[4-(4-pyridyl)-piperazin-1-yl]carbonylamino]piperidino]-propionate

To a solution of 2 g (0.0069 Mol) of 4-[[4-(4-pyridyl)-piperazin-1-yl]carbonylamino]piperidine in 30 ml of methanol are added 0.6 g (0.0069 Mol) of methyl acrylate (0.7 ml) and the mixture is left to stand at ambient temperature for 4 hours. It is then evaporated to dryness in vacuo and the residue is purified over a silica gel column, using methylene chloride/methanol/conc. ammonia=9:5:0.05 as eluant.

Yield: 1.5 g (77.1% of theory), Colourless solid.

Mass spectrum: M$^+$=375

R$_f$ value: 0.38 (silica gel; methylene chloride/methanol/conc. ammonia=9:1:0.1)

The following compound is prepared analogously to Example 7:

(1) Methyl 4-[[4-(4-pyridyl)-piperazin-1-yl]-ethylcarbonyl]phenoxy-acetate hydrochloride Prepared from 1-(4-pyridyl)-piperazine and methyl 4-acryloylphenoxy-acetate.

Example 8

Methyl N-[4-(4-pyridyl)-piperazin-1-yl]carbonyl]-3-(4-piperidinyl)-propionate-hydrochloride A mixture of 9 g (0.134 Mol) of methyl 4-(4-nitrophenyloxycarbonyl)-3-(4-piperidinyl)-propionate, 2.2 g (0.0134 Mol) of 1-(4-pyridyl)-piperazine and N-ethyldiisopropylamine is heated to 140° C. for 4 hours and then cooled, triturated with ether and decanted off. The solid matter is partitioned between ethyl acetate and water, the organic phase is washed with 1N sodium hydroxide solution and then with water, dried and evaporated to dryness in vacuo. The residue is purified over a silica gel column, using methylene chloride with 2.5, 3 and 5% methanol as eluant. The yellow residue is dissolved in ether. This solution is acidifed with ethereal hydrochloric acid. The solid precipitated is suction filtered.

Yield: 1.5 g (28.2% of theory),

Melting point: >320° C.

Mass spectrum: M$^+$=360

R$_f$ value: 0.57 (silica gel; methylene chloride/methanol= 9:1)

The following compounds may be prepared analogously to Example 8:

(1) N-Methyl-N-[4-[[4-(4-pyridyl)-piperazin-1-yl]carbonyl]piperidinyl]-β-alanine methyl ester Prepared from N-methyl-N-[4-[1-(4-nitrophenyloxycarbonyl)piperidinyl]-β-alanine methyl ester and 1-(4-pyridyl)piperazine.

(2) N-Acetyl-N-[4-[[4-(4-pyridyl)-piperazin-1-yl]carbonyl]piperidinyl]-β-alanine methyl ester Prepared from N-acetyl-N-[4-[1-(4-nitrophenyloxycarbonyl)piperidinyl]]-β-alanine methyl ester and 1-(4-pyridyl)piperazine.

(3) N-Methyl-N-[4-[[4-(4-pyridyl)-piperazin-1-yl]carbonyl]piperidinyl]glycine methyl ester dihydrochloride Prepared from N-methyl-N-[4-[1-(4-nitrophenyloxycarbonyl)piperidinyl]]glycine methyl ester and 1-(4-pyridyl)-piperazine.

(4) N-Acetyl-N-[4-[[4-(4-pyridyl)-piperazin-1-yl]carbonyl]piperidinyl]glycine methyl ester Prepared from N-acetyl-N-[4-[1-(4-nitrophenyloxycarbonyl)piperidinyl]]glycine methyl ester and 1-(4-pyridyl)-piperazine.

(5) N-(2-Phenylethyl)-N-[4-[[4-(4-pyridyl)-piperazin-1-yl]carbonyl]piperidinyl]-β-alanine methyl ester Prepared from N-(2-phenylethyl)-N-[4-[1-(4-nitrophenyloxycarbonyl)-piperidinyl]]-β-alanine methyl ester and 1-(4-pyridyl)-piperazine.

(6) Methyl N-[[4-(4-pyridyl)-piperazin-1-yl]carbonyl]-4-(4-piperidinyl)-butyrate hydrochloride Prepared from methyl N-(4-nitrophenyloxycarbonyl)-4-(4-piperidinyl)-butyrate and 1-(4-pyridyl)-piperazine.

Melting point: 112°–115° C. (Decomp.)

$R_f$ value: 0.45 (silica gel; methylene chloride/methanol=9:1)

(7) [3-[[4-(4-Pyridyl)-piperazin-1-yl]carbonylamino]phenyl]propionic acid hydrochloride Prepared from methyl 3-[4-[4-nitrophenyloxycarbonylamino]phenyl]-propionate, 1-(4-pyridyl)-piperazine and triethylamine.

(8) Ethyl N-[[4-(4-pyridyl)-piperazin-1-yl]carbonyl]-3-(piperidin-4-yloxy)-propionate hydrochloride Prepared from ethyl N-(4-nitro-phenyloxycarbonyl)-(3-piperidin-4-yloxy)-propionate and 1-(4-pyridyl)-piperazine.

Melting point: 105°–106° C. (Decomp.)

Mass spectrum: $M^+$=390

$R_f$ value: 0.18 (silica gel; methylene chloride/methanol=9:1)

Example 9

N-[4-[[4-(4-Pyridyl)-piperazin-1-yl]carbonyl]piperidinyl]-β-alanine methyl ester-dihydrochloride To a solution of 1.6 g (0.034 Mol) of N-tert.butyloxycarbonyl-N-[4-[[4-(4-pyridyl)-piperazin-1-yl]carbonyl]piperidinyl]-β-alanine methyl ester in 20 ml of methylene chloride are added, at ambient temperature, and with stirring, 10 ml of trifluoroacetic acid and the mixture is left to stand for 3 hours. It is then evaporated down in vacuo, the residue is mixed with acetone and again evaporated to dryness. The residue is dissolved in methanol, acidified with ethereal hydrochloric acid and again evaporated to dryness in vacuo. The solid residue remaining is triturated with acetone. The solid matter is suction filtered and dried. Yield: 1.37 g (90.7% of theory), Melting point: 204°–207° C. (Decomp.)

$R_f$ value: 0.16 (silica gel; methylene chloride/methanol=9:1)

The following compound may be prepared analogously to Example 9:

(1) N-[4-[[4-(4-Pyridyl)-piperazin-1-yl]carbonyl]piperidinyl]glycine methyl ester dihydrochloride Prepared from N-tert.butyloxycarbonyl-N-[4-[[4-(4-pyridyl)piperazin-1-yl]carbonyl]piperidinyl]glycine methyl ester.

Example 10

Cyclohexyl 3-[4-[4-(4-pyridyl)-piperazin-1-yl]carbonylamino]piperidino-propionate-dihydrochloride A weak current of hydrogen chloride gas is passed through a suspension of 300 mg (0.7 mMol) of 3-[4-[4-(4-pyridyl)piperazin-1-yl]carbonylamino]piperidino-propionic acid dihydrochloride in 20 ml of cyclohexanol for half an hour. It is then left to stand overnight at ambient temperature and then heated for a further 2 hours to reflux temperature. After cooling, it is poured onto ether and the precipitate is suction filtered.

The following compounds may be prepared analogously to Example 10:

(1) Isobutyl 3-[4-[4-(4-pyridyl)-piperazin-1-yl]carbonylamino]piperidino-propionate dihydrochloride Prepared from 3-[4-[4-(4-pyridyl)-piperazin-1-yl]carbonylamino]piperidino-propionic acid dihydrochloride and isobutanol.

(2) Isobutyl[4-[4-(4-pyridyl)-piperazino-1-yl]carbonylamino]piperidino-acetate dihydrochloride Prepared from [4-[4-(4-pyridyl)-piperazin-1-yl]carbonylamino]piperidino-acetic acid and isobutanol.

(3) Cyclohexyl[4-[4-(4-pyridyl)-piperazino-1-yl]carbonylamino]piperidino-acetate dihydrochloride Prepared from [4-[4-(4-pyridyl)-piperazin-1-yl]carbonylamino]piperidino acetic acid and cyclohexanol.

(4) Cyclohexyl[4-trans-[[4-(4-pyridyl)-piperazin-1-yl]acetyl]amino]-cyclohexane-carboxylate dihydrochloride Prepared from [4-trans-[[4-(4-pyridyl)-piperazin-1-yl]-acetyl]amino]cyclohexanecarboxylic acid and cyclohexanol.

$R_f$ value: 0.23 (silica gel; methylene chloride/methanol/conc. ammonia=9:1:0.1)

Mass spectrum: $M^+$=428

(5) Isobutyl[4-trans-[[4-(4-pyridyl)-piperazin-1-yl]acetyl]amino]-cyclohexane-carboxylate dihydrochloride Prepared from [4-trans-[[4-(4-pyridyl)-piperazin-1-yl]acetyl]amino]cyclohexane-carboxylic acid and isobutanol.

$R_f$ value: 0.22 (silica gel; methylene chloride/methanol/conc. ammonia=9:1:0.1)

Mass spectrum: $M^+$=402

Example 11

Pivaloyloxymethyl 3-[4-[4-(4-pyridyl)-piperazin-1-yl]carbonylamino]piperidinopropionate A mixture of equimolar parts of 3-[4-[4-(4-pyridyl)-piperazin-1-yl]carbonylamino]piperidinopropionic acid, chloromethyl pivaloate, potassium iodide and potassium carbonate is stirred in dimethylformamide at ambient temperature for 2 days. It is then poured into water and extracted with ethyl acetate. The combined organic phases are dried and evaporated to dryness in vacuo. The remaining residue is purified by chromatography over a silica gel column.

The following compound may be prepared analogously to Example 11:

(1) (1-Ethyloxy)-carbonyloxyethyl 3-[4-[4-(4-pyridyl)piperazin-1-yl]carbonylamino]piperidinopropionate Prepared from 3-[4-[4-(4-pyridyl)-piperazin-1-yl]carbonylamino]piperidinopropionic acid and 1-chloroethylethylcarbonate.

Example 12

[4-trans-[2S-[4-(4-Pyridyl)-piperazin-1-yl]propionyl]amino]cyclohexane-carboxylic acid dihydrochloride An equimolar solution of methyl 4-trans-(L-alanyl)-aminocyclohexane-carboxylate trifluoroacetate and 4-pyridyl-N,N-bis-(2-chlorethyl)amine hydrochloride is heated together with 8 Mol of N-ethyl-diisopropylamine in ethanol to reflux temperature for 20 hours. The solution is then evaporated down under reduced pressure and the residue is partitioned between water and ethyl acetate. The residue remaining after drying and evaporation is purified by chromatography.

The following compounds are prepared analogously to Example 12:

(1) Methyl[4-trans-[2S-[4-(4-pyridyl)-piperazin-1-yl]-(3-(4-methoxyphenyl)-propionyl)]amino]cyclohexane-carboxylate dihydrochloride Prepared from methyl 4-trans-(O-methyl-L-tyrosyl)-aminocyclohexane-carboxylate trifluoroacetate, 4-pyridyl-N,N-bis-(2-chloroethyl)amine hydrochloride and N-ethyldiisopropylamine.

(2) Methyl N-[2S-[4-(4-pyridyl)-piperazin-1-yl]-propionyl] (piperidin-4-yloxy)-acetate dihydrochloride Prepared from methyl N-(L-alanyl)-4-piperidinyloxy-acetate trifluoroacetate, 4-pyridyl-N,N-bis-(2-chloroethyl) amino hydrochloride and N-ethyl-diisopropylamine.

(3) Methyl N-[2S-[4-(4-pyridyl)-piperazin-1-yl]-(3-(4-methoxyphenyl)-propionyl)]-(piperidin-4-yloxy)-acetate dihydrochloride Prepared from methyl N-(O-methyl-L-tyrosyl)-4-piperidinyloxyacetate trifluoroacetate, 4-pyridyl-N,N-bis-(2-chloroethyl)amino hydrochloride and N-ethyl-diisopropylamine.

Example 13

Dry ampoule containing 2.5 mg of active substance per 1 ml

Composition:

| Active substance | 2.5 mg |
|---|---|
| Mannitol | 50.0 mg |
| Water for injections ad | 1.0 ml |

Preparation:

The active substance and mannitol are dissolved in water. After transferring the solution to the ampoule, it is freeze-dried.

At the point of use, the solution is made up with water for injections.

Example 14

Dry ampoule containing 35 mg of active substance per 2 ml

Composition:

| Active substance | 35.0 mg |
|---|---|
| Mannitol | 100.0 mg |
| Water for injections ad | 2.0 ml |

Preparation:

The active substance and mannitol are dissolved in water. After transferring the solution to the ampoule, it is freeze-dried.

At the point of use, the solution is made up with water for injections.

Example 15

Tablet containing 50 mg of active substance

Composition:

| (1) Active substance | 50.0 mg |
|---|---|
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granules. From this mixture, compressed tablets are produced, biplanar, facetted on both sides and notched on one side. Diameter of tablets: 9 mm.

Example 16

Tablet containing 350 mg of active substance

Composition:

| (1) Active substance | 350.0 mg |
|---|---|
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granules. From this mixture, compressed tablets are produced, biplanar, facetted on both sides and notched on one side. Diameter of tablets: 12 mm.

Example 17

Capsules containing 50 mg of active substance

Composition:

| (1) Active substance | 50.0 mg |
|---|---|
| (2) Dried corn starch | 58.0 mg |
| (3) Powdered lactose | 50.0 mg |
| (4) Magnesium stearate | 2.0 mg |
| | 160.0 mg |

Preparation:

(1) is triturated with (3). This triturate is added to the mixture of (2) and (4), with thorough mixing.

This powdered mixture is packed into size 3 hard gelatin oblong capsules in a capsule filling machine.

Example 18

Capsules containing 350 mg of active substance

Composition:

| (1) Active substance | 350.0 mg |
|---|---|
| (2) Dried corn starch | 46.0 mg |
| (3) Powdered lactose | 30.0 mg |
| (4) Magnesium stearate | 4.0 mg |
| | 430.0 mg |

Preparation:

(1) is triturated with (3). This triturate is added to the mixture of (2) and (4), with thorough mixing.

This powdered mixture is packed into size 0 hard gelatin oblong capsules in a capsule filling machine.

What is claimed is:

1. A piperazine derivative of the formula

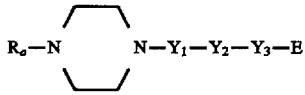

(I)

wherein $R_a$ denotes a pyridyl group, $Y_1$ denotes a $-CO-$, $-CO-CO-$, $-A_1-CO-$, $-C-A_1-$, $-SO_2-A_2-$, $-A_2-SO_2-$, $-CO-$ $A_1$—CO—, —CO—$NR_1$—CO—, —CO—$NR_1$—$A_2$—, —CO—$NR_1$—$A_2$—CO— or —CO—$A_2$—$NR_1$—CO— group, wherein $R_1$ denotes a hydrogen atom, a $C_{1-5}$-alkyl-, aryl- or aryl-$C_{1-3}$-alkyl group, $A_1$ denotes an n-$C_{1-5}$-alkylene group optionally substituted by a $C_{1-5}$-alkyl-, cyclohexyl-$C_{1-3}$-alkyl-, aryl- or aryl-$C_{1-3}$-alkyl group or an $R_1O$=— group, provided that this is not in the a-position to a nitrogen atom, and $A_2$ denotes an n-$C_{1-4}$-alkylene group optionally substituted by a $C_{1-5}$-alkyl, aryl or aryl-$C_{1-3}$-alkyl group, $Y_2$ denotes an —$NR_1$—B— group, the link to the $Y_1$ group being effected via the nitrogen atom of the —$NR_1$— group, wherein $R_1$ is as hereinbefore defined and B denotes a phenylene or cyclohexylene group, $Y_3$ denotes a —CO—, —$A_2$—CO—, —$CH_2$—CH($NHR_2$)—CO—, —$NR_2$—$A_3$—CO—, —O—$A_3$—CO— or —CO—$A_3$—CO— group, wherein $R_1$ and $A_2$ are as hereinbefore defined, $A_3$ denotes an n-$C_{1-3}$-alkylene group optionally substituted by a $C_{1-5}$-alkyl, aryl or aryl-$C_{1-3}$-alkyl group and $R_2$ denotes a hydrogen atom, a $C_{1-5}$-alkyl, aryl-$C_{1-3}$-alkyl, aryl, $C_{1-5}$-alkoxycarbonyl, $C_{1-5}$-alkanoyl, $C_{1-5}$-alkylsulphonyl, aryl-$C_{1-3}$-alkylsulphonyl or arylsulphonyl group, a formyl group optionally substituted by an aryl- or aryl-$C_{1-3}$-alkyl group, and the —$A_2$—CO— group is linked to the group $Y_2$ via the group $A_2$, the —$NR_2$—$A_3$—CO— group is linked to the group $Y_2$ via the —$NR_2$— group and the —O—$A_3$—CO— group is linked to the group $Y_2$ via the oxygen atom, but an —$NR_2$— or —O—$A_3$—CO— group cannot be linked to a nitrogen atom of the group $Y_2$, and E denotes a hydroxy group, a $C_{1-6}$-alkoxy group, a phenylalkoxy group wherein the alkoxy moiety may contain 1 to 3 carbon atoms, a $C_{3-9}$-cycloalkoxy group, wherein the $C_{5-8}$-cycloalkyl moiety may additionally be substituted by one or two $C_{1-3}$-alkyl groups, a $C_{5-8}$-cycloalkoxy group wherein a methylene group in the 3- or 4-position of the cycloalkyl moiety is replaced by an oxygen atom or by an imino group optionally substituted by an alkyl, phenylalkyl or phenylalkoxycarbonyl group, wherein the alkyl and alkoxy moieties may each contain 1 to 3 carbon atoms, or by a $C_{2-6}$-alkanoyl group, and the cycloalkyl moiety may additionally be substituted by one or two $C_{1-3}$-alkyl groups, a cycloalkenyloxy group wherein the cycloalkenyl moiety may contain 4 to 7 carbon atoms, an alkenyloxy, phenylalkenyloxy, alkynyloxy or phenylalkynyloxy group, with the proviso that no bond to the oxygen atom starts from a carbon atom carrying a double or triple bond, and wherein the alkenyl and alkynyl moieties may each contain 3 to 5 carbon atoms, a cycloalkylalkoxy group, wherein the cycloalkyl moiety may contain 3 to 8 carbon atoms and the alkoxy moiety may contain 1 to 3 carbon atoms, a bicycloalkoxy group having a total of 8 to 10 carbon atoms which may additionally be substituted in the bicycloalkyl moiety by one or two $C_{1-3}$-alkyl groups, a 1,3-dihydro-3-oxo-1-isobenzofuranyloxy group or an $R_5$—CO—O—($R_3CR_4$)—O— group, wherein $R_3$ denotes a hydrogen atom, a $C_{1-6}$-alkyl, $C_{3-7}$-cycloalkyl or phenyl group, $R_4$ denotes a hydrogen atom or a $C_{1-6}$-alkyl group and $R_5$ denotes a $C_{1-5}$-alkyl, $C_{1-5}$-alkoxy, $C_{5-7}$-cycloalkyl or $C_{5-7}$-cycloalkoxy group, or E denotes an a-amino group of a natural amino acid and the esters thereof, whilst by the terms "an aryl group", "a phenyl group" or "a phenylene group" mentioned in the definitions of the above groups, is meant a phenyl or phenylene group optionally mono-, di- or trisubstituted by fluorine, chlorine, bromine or iodine atoms, or by alkyl, trifluoromethyl, nitro, amino, alkylamino, dialkylamino, alkanoylamino, hydroxy, alkoxy, carboxy, alkoxycarbonyl, hydroxycarbonylalkoxy, alkoxycarbonylalkoxy, aminocarbonyl, alkylaminocarbonyl or dialkylaminocarbonyl groups, wherein the substituents may be identical or different and the above-mentioned alkyl and alkoxy moieties may each contain 1 to 3 carbon atoms, and by the esters of a natural a-amino group are meant the $C_{1-6}$-alkyl, $C_{2-6}$-alkenyl, $C_{5-7}$-cycloalkyl, phenyl or phenyl-$C_{1-3}$-alkylesters, or a tautomer or pharmaceutically acceptable salt thereof.

2. A piperazine derivative of the formula I according to claim 1, wherein $R_a$ denotes a 3- or 4-pyridyl group, $Y_1$ denotes a —CO—, —CO—CO—, —$A_1$—CO—, —CO—$A_1$— or —CO—$A_1$—CO— group, wherein $A_1$ denotes an n-$C_{1-5}$-alkylene group optionally substituted by a $C_{1-5}$-alkyl, phenyl or phenyl-$C_{1-3}$-alkyl group, wherein the phenyl nuclei of the above-mentioned phenyl and phenylalkyl groups may each additionally be substituted by a hydroxy or methoxy group, $Y_2$ denotes an —$NR_1$—B— group, the link to the $Y_1$ group being effected via the nitrogen atom of the —$NR_1$— group and $R_1$ denotes a hydrogen atom, a $C_{1-5}$-alkyl, phenyl or phenyl-$C_{1-3}$-alkyl group and B denotes a 1,3-phenylene, 1,4-phenylene, 1,3-cyclohexylene or 1,4-cyclohexylene group, $Y_3$ denotes a —CO—, —$A_2$—CO—, —$NR_2$—$A_3$—CO— or —O—$A_3$—CO— group, wherein $A_2$ denotes an n-$C_{1-4}$-alkylene group optionally substituted by a $C_{1-5}$-alkyl, phenyl or phenyl-$C_{1-3}$-alkyl group, $A_3$ denotes an n-$C_{1-3}$-alkylene group optionally substituted by a $C_{1-5}$-alkyl, phenyl or phenyl-$C_{1-3}$-alkyl group and $R_2$ denotes a hydrogen atom, a $C_{1-5}$-alkyl, phenyl-$C_{1-3}$-alkyl, phenyl, $C_{1-5}$-alkoxycarbonyl or $C_{1-5}$-alkanoyl group, and the —$A_2$—CO— group is linked to the group $Y_2$ via the group $A_2$, the —$NR_2$—$A_3$—CO— group is linked to the group $Y_2$ via the —$NR_2$— group and the —O—$A_3$—CO— group is linked to the group $Y_2$ via the oxygen atom, but an —$NR_2$— or —O—$A_3$—CO— group may not be linked to a nitrogen atom of the group $Y_2$, and E denotes a hydroxy group, a $C_{1-6}$-alkoxy group, a phenylalkoxy group wherein the alkoxy moiety may contain 1 to 3 carbon atoms, a $C_{4-7}$-cycloalkoxy group or an $R_5$—CO—O—($R_3CR_4$)—O— group wherein $R_3$ denotes a hydrogen atom, a $C_{1-6}$-alkyl, $C_{3-7}$-cycloalkyl or phenyl group, $R_4$ denotes a hydrogen atom or a $C_{1-6}$-alkyl group and $R_5$ denotes a $C_{1-5}$-alkyl, $C_{1-5}$-alkoxy, $C_{5-7}$-cycloalkyl or $C_{5-7}$-cycloalkoxy group, or E denotes an a-amino group of a natural amino acid or the esters thereof or a tautomer or pharmaceutically acceptable salt thereof.

3. A piperazine derivative of the formula I according to claim 1, wherein $R_a$ denotes a 4-pyridyl group, $Y_1$ denotes a —CO—, —CO—CO—, —$A_1$—CO—, —CO—$A_1$— or —CO—$A_1$—CO— group, wherein $A_1$ denotes an n-$C_{1-5}$-alkylene group optionally substituted by a $C_{1-5}$-alkyl, phenyl or phenyl-$C_{1-2}$-alkyl group, wherein the phenyl nuclei of the above-mentioned phenyl and phenylalkyl groups may each additionally be substituted by a hydroxy or methoxy group, $Y_2$ denotes an —$NR_1$—B— group, the $Y_1$ group being linked via the nitrogen atom of the —$NR_1$— group and $R_1$ denotes a hydrogen atom, a $C_{1-5}$-alkyl, phenyl or phenyl-$C_{1-2}$-alkyl group and B denotes a 1,3-phenylene, 1,4-phenylene, 1,3-cyclohexylene or 1,4-cyclohexylene group, $Y_3$ denotes a —CO—, —$A_2$—CO—, —$NR_2$—$A_3$—CO— or —O—$A_3$—CO— group, wherein $A_2$ denotes an n-$C_{1-4}$-alkylene group optionally substituted by a $C_{1-3}$-alkyl, phenyl or phenyl-$C_{1-2}$-alkyl group, $A_3$ denotes an n-$C_{1-3}$-alkylene group optionally substituted by a $C_{1-5}$-alkyl, phenyl or phenyl-$C_{1-3}$-alkyl group and $R_2$ denotes a hydrogen atom, a $C_{1-3}$-alkyl, $C_{1-5}$-alkoxycarbonyl or $C_{1-3}$-alkanoyl group, and the —$A_2$—CO— group is linked to the group $Y_2$ via the group $A_2$, the —$NR_2$—$A_3$—CO— group is linked to the group $Y_2$ via the —$NR_2$— group and the —O—$A_3$—CO— group is linked to the group $Y_2$ via the oxygen atom, but an —$NR_2$— or —O—$A_3$—CO— group cannot be linked to a nitrogen atom of the group $Y_2$, and E denotes a hydroxy group, a $C_{1-5}$-alkoxy group, a $C_{5-7}$-cycloalkoxy group or an $R_5$—CO—O—($R_3CR_4$)—O— group, wherein $R_3$ denotes a hydrogen atom, a $C_{1-3}$-alkyl or $C_{5-7}$-cycloalkyl group, $R_4$ denotes a hydrogen atom and $R_5$ denotes a $C_{1-5}$-alkyl or $C_{1-3}$-alkoxy group, or E denotes an a-amino group of a natural amino acid or the esters thereof with a $C_{1-6}$-alkanol or benzylalcohol, or a tautomer or pharmaceutically acceptable salt thereof.

4. A piperazine derivative of the formula I according to claim 1, wherein $R_a$ denotes a 4-pyridyl group, $Y_1$ denotes a —CO—, —COCO—, —$A_1$—CO—, —CO—$A_1$— or —CO—$CH_2$—CO— group, wherein $A_1$ denotes an n-$C_{1-4}$-alkylene group optionally substituted by a methyl or methoxyphenyl group, $Y_2$ denotes an —$NR_1$—B— group, the link with the $Y_1$ group being effected via the nitrogen atom of the —$NR_1$— group and $R_1$ denotes a hydrogen atom and B denotes a 1,3-phenylene, 1,4-phenylene, 1,3-cyclohexylene or 1,4-cyclohexylene group, $Y_3$ denotes a —CO—, —$A_2$—CO—, —$NR_2$—$A_3$—CO— or —O—$A_3$—CO— group, wherein $A_2$ denotes an n-$C_{1-3}$-alkylene group, $A_3$ denotes a $C_{1-2}$-alkylene group and $R_2$ denotes a hydrogen atom, a methyl, benzyl, phenylethyl or acetyl group, and the —$A_2$—CO— group is linked to the group $Y_2$ via the group $A_2$, the —$NR_2$—$A_3$—CO— group is linked to the group $Y_2$ via the —$NR_2$— group and the —O—$A_3$—CO— group is linked to the group $Y_2$ via the oxygen atom, but an —$NR_2$— or —O—$A_3$—CO— group cannot be linked to a nitrogen atom of the group $Y_2$, and E denotes a hydroxy group, a $C_{1-4}$-alkoxy group, a $C_{5-7}$-cycloalkoxy group or an $R_5$—CO—O—($R_3CR_4$)—O— group, wherein $R_3$ denotes a hydrogen atom or a $C_{1-3}$-alkyl group, $R_4$ denotes a hydrogen atom and $R_5$ denotes a $C_{1-5}$-alkyl or $C_{1-3}$-alkoxy group, or E denotes a glycinyl group or the methyl esters thereof, or a tautomer or pharmaceutically acceptable salt thereof.

5. A compound selected from the group consisting of:

(a) [4-trans-[3-[4-(4-Pyridyl)-piperazin-1-yl]propionyl]amino]-cyclohexanecarboxylic acid, (b) 3-[4-trans-[4-(4-Pyridyl)-piperazin-1-yl]carbonylamino]-cyclohexylpropionic acid, (c) 3-[4-trans-[4-(4-Pyridyl)-piperazin-1-yl]malonylamino]cyclohexylcarboxylic acid, (d) Methyl[4-trans-[3-[4-(4-pyridyl)-piperazin-1-yl]-propionyl]-amino]cyclohexane carboxylate, (e) Methyl 3-[4-trans-[4-(4-pyridyl)-piperazin-1-yl]-carbonylamino]cyclohexyl propionate, (f) Methyl[4-trans-[4-(4-pyridyl)-piperazin-1-yl]-malonylamino]-cyclohexyl carboxylate, (g) Cyclohexyl[4-trans-[[4-(4-pyridyl)-piperazin-1-yl]-acetyl]-amino]-cyclohexane carboxylate, (h) Isobutyl[4-trans-[[4-(4-pyridyl)-piperazin-1-yl]-acetyl]-amino]-cyclohexane carboxylate, and the tautomers and pharmaceutically acceptable salts thereof.

6. A pharmaceutical composition suitable comprising a compound in accordance with claims 1, 2, 3, 4 or 5.

7. A method for treating or preventing inflammation which comprises administering to a host suffering from or suscepticle to inflammation an anti-inflammatory amount of a compound in accordance with claims 1, 2, 3, 4 or 5.

8. A method for treating or preventing bone degradation which comprises administering to a host suffering from or suscepticle to bone degradation a therapeutic amount of a compound in accordance with claims 1, 2, 3, 4 or 5.

9. A method for treating or preventing thrombosis which comprises administering to a host suffering from or suscepticle to thrombosis an anti-thrombotic amount of a compound in accordance with claims 1, 2, 3, 4 or 5.

10. A method for treating or preventing tumor metastasis which comprises administering to a host suffering from or suscepticle to tumor metastasis a therapeutic amount of a compound in accordance with claims 1, 2, 3, 4 or 5.

11. A method for treating a disease in a warm-blooded animal in which smaller or larger cell-aggregates occur or cell-matrix interactions are involved which comprises administering to said animal a therapeutically effective amount of a compound as recited in claim 1.

* * * * *